United States Patent
Adachi et al.

(10) Patent No.: US 8,351,658 B2
(45) Date of Patent: Jan. 8, 2013

(54) EYELID DETECTION APPARATUS AND PROGRAMS THEREFOR

(75) Inventors: Jun Adachi, Obu (JP); Yukihiko Yoshinaga, Kariya (JP); Tomoharu Suzuki, Anjo (JP); Takashi Hiramaki, Nagoya (JP); Kenichi Ogawa, Kariya (JP); Kenichi Ohue, Toyota (JP); Kentaro Takahashi, Toyota (JP); Shigeyasu Uozumi, Toyota (JP); Shinichi Kojima, Nisshin (JP); Satoru Nakanishi, Aichi-ken (JP)

(73) Assignees: Aisin Seiki Kabushiki Kaisha, Aichi-ken (JP); Toyota Jidosha Kabushiki Kaisha, Aichi-ken (JP)

( * ) Notice: Subject to any disclaimer, the term of this patent is extended or adjusted under 35 U.S.C. 154(b) by 1351 days.

(21) Appl. No.: 12/026,959

(22) Filed: Feb. 6, 2008

(65) Prior Publication Data

US 2008/0212850 A1   Sep. 4, 2008

(30) Foreign Application Priority Data

Feb. 8, 2007 (JP) ................................. 2007-028822

(51) Int. Cl.
*G06K 9/00* (2006.01)
(52) U.S. Cl. .......................... 382/117; 382/199; 382/203
(58) Field of Classification Search .................. 345/156, 345/473, 629; 382/103, 118, 305, 117, 199, 382/203
See application file for complete search history.

(56) References Cited

U.S. PATENT DOCUMENTS

| 5,432,866 | A |   | 7/1995  | Sakamoto |
| 5,455,601 | A | * | 10/1995 | Ozaki ............................ 345/156 |
| 5,795,306 | A | * | 8/1998  | Shimotani et al. ............ 600/558 |
| 6,130,617 | A |   | 10/2000 | Yeo |
| 6,243,015 | B1 |  | 6/2001  | Yeo |
| 6,304,187 | B1 |  | 10/2001 | Pirim |
| 6,535,223 | B1 | * | 3/2003  | Foley ............................ 345/629 |
| 6,606,397 | B1 |  | 8/2003  | Yamamoto |
| 6,717,518 | B1 |  | 4/2004  | Pirim et al. |
| 6,885,760 | B2 |  | 4/2005  | Yamada et al. |
| 7,043,056 | B2 | * | 5/2006  | Edwards et al. .............. 382/103 |
| 7,203,340 | B2 | * | 4/2007  | Gorodnichy ................... 382/103 |
| 7,466,847 | B2 | * | 12/2008 | Komura ......................... 382/118 |
| 7,689,010 | B2 | * | 3/2010  | Canzler et al. ................ 382/118 |
| 7,835,568 | B2 | * | 11/2010 | Park et al. ...................... 382/154 |
| 7,894,637 | B2 | * | 2/2011  | Noguchi et al. .............. 382/118 |
| 8,150,205 | B2 | * | 4/2012  | Watanabe ..................... 382/276 |
| 2003/0169907 | A1 | * | 9/2003 | Edwards et al. .............. 382/118 |

(Continued)

FOREIGN PATENT DOCUMENTS

CN          1299498 A      6/2001

(Continued)

OTHER PUBLICATIONS

European Search Report dated Jul. 9, 2008.

(Continued)

*Primary Examiner* — Gregory M Desire
(74) *Attorney, Agent, or Firm* — Sughrue Mion, PLLC

(57) ABSTRACT

An eyelid detection apparatus includes a face image storing means storing a plurality of face images of a subject captured at different timings, a change detecting means detecting changes in each face image caused by blinking after processing the plurality of face images stored by the face image storing means, and an eyelid detecting means detecting a position of an eyelid of the subject based on the changes detected by the change detecting means.

9 Claims, 20 Drawing Sheets

U.S. PATENT DOCUMENTS

| | | | |
|---|---|---|---|
| 2004/0179716 A1 | 9/2004 | Tafuki et al. | |
| 2005/0199783 A1* | 9/2005 | Wenstrand et al. | 250/214.1 |
| 2006/0204042 A1 | 9/2006 | Hammoud et al. | |
| 2007/0153005 A1* | 7/2007 | Asai | 345/473 |
| 2007/0172155 A1* | 7/2007 | Guckenberger | 382/305 |
| 2007/0201724 A1* | 8/2007 | Steinberg et al. | 382/103 |
| 2008/0212850 A1* | 9/2008 | Adachi et al. | 382/118 |
| 2010/0014759 A1 | 1/2010 | Suzuki et al. | |

FOREIGN PATENT DOCUMENTS

| | | |
|---|---|---|
| EP | 1 701 289 A1 | 9/2006 |
| FR | 2 784 887 A1 | 4/2000 |
| JP | 10-063850 A | 3/1998 |
| JP | 2000-123188 A | 4/2000 |
| JP | 2000-137792 A | 5/2000 |
| JP | 2001-216515 A | 8/2001 |
| JP | 2003-158643 A | 5/2003 |
| JP | 2004-192552 A | 7/2004 |
| JP | 2004-220080 A | 8/2004 |
| JP | 2004-234494 A | 8/2004 |
| WO | 00/24309 A1 | 5/2000 |
| WO | 2004/034905 A1 | 4/2004 |

OTHER PUBLICATIONS

Chinese Office Action issued in Chinese Application No. 200810005812X dated Mar. 23, 2011.

Japanese Office Action issued in Japanese Application No. 2007-028822 dated Jun. 14, 2011.

Office Action issued in U.S. Appl. No. 12/517,509 dated Aug. 30, 2012.

* cited by examiner

| -1 | 0 | 1 |
|---|---|---|
| -2 | 0 | 2 |
| -1 | 0 | 1 |

Operator for transverse edge detection

- - - - : Minus edge (bright → dark)
——— : Plus edge (dark → bright)

Latest normalized image
F I G. 14 A
  
Image accumulated 66 ms ago | Image accumulated 99 ms ago | Image accumulated 132 ms ago
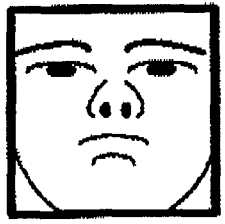  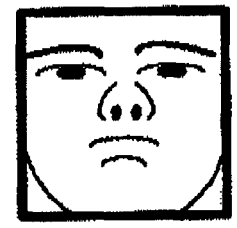
F I G. 14 B    F I G. 14 C    F I G. 14 D
  
  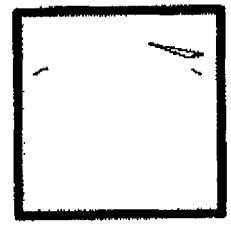
F I G. 14 E    F I G. 14 F    F I G. 14 G
Difference image This portion is eliminated as the area is larger than a threshold value
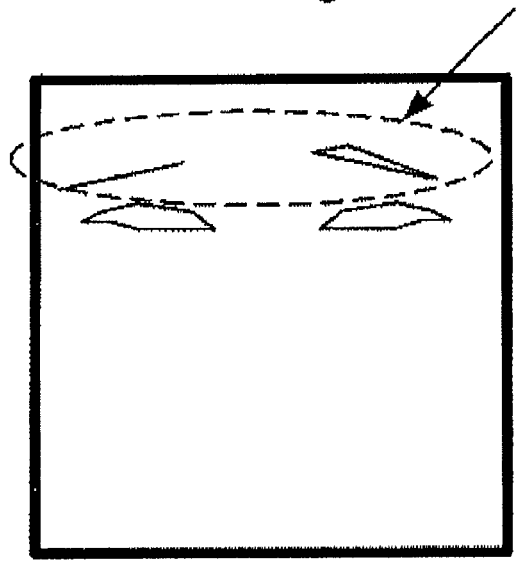
F I G. 15 A
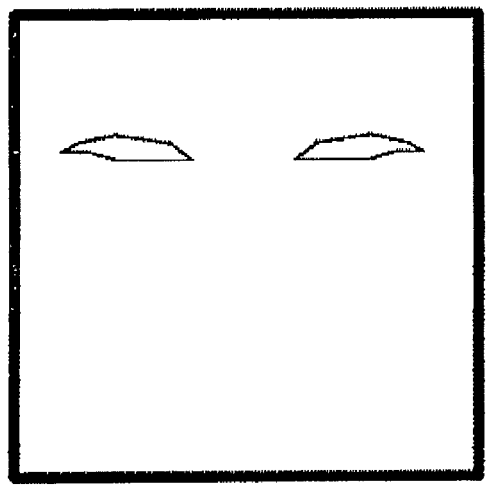
F I G. 15 B F I G. 16 A
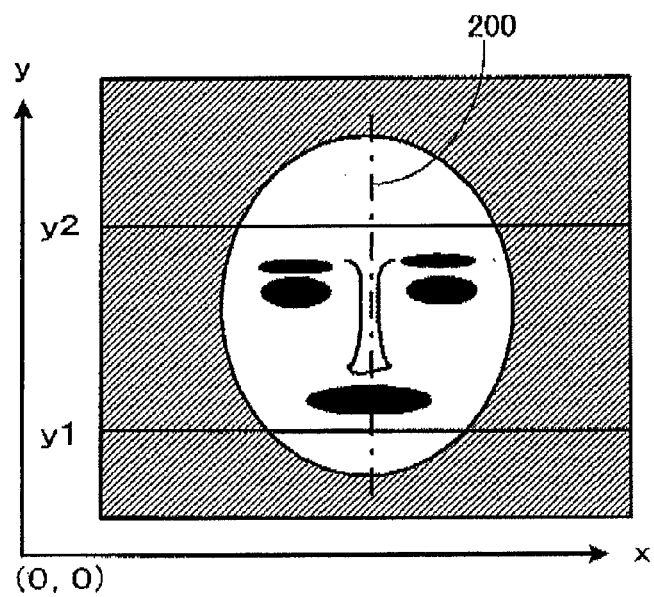
F I G. 16 B
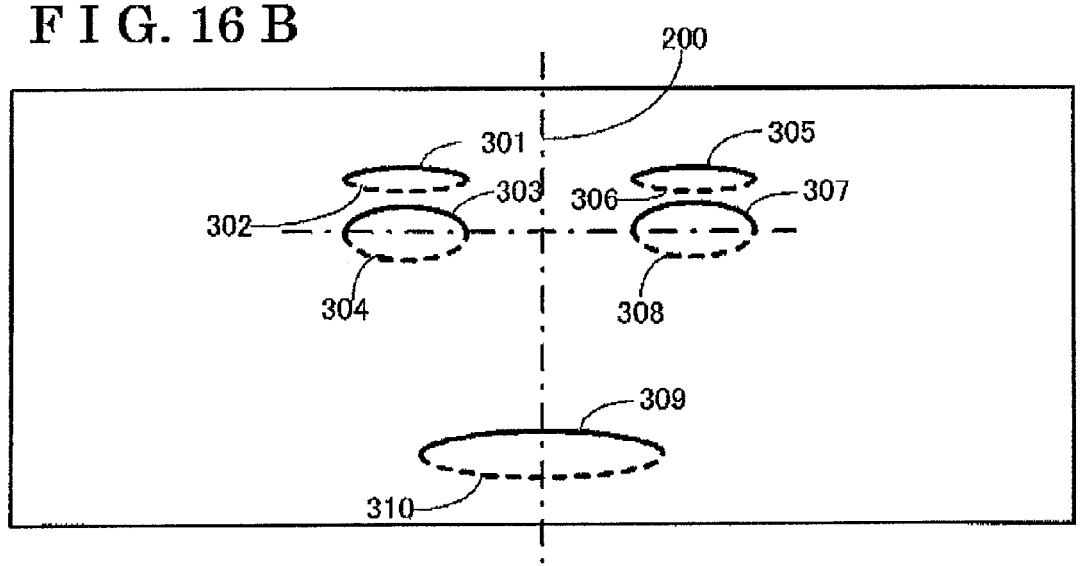

EYELID DETECTION APPARATUS AND PROGRAMS THEREFOR

CROSS REFERENCE TO RELATED APPLICATIONS

This application is based on and claims priority under 35 U.S.C §119 with respect to Japanese Patent Application 2007-028822, filed on Feb. 8, 2007, the entire content of which is incorporated herein by reference.

FIELD OF THE INVENTION

This invention relates to an eyelid detection apparatus and programs therefor.

BACKGROUND

There is a known technology which detects positions of a human face or eyes in an image including the human face. For example, a face detection apparatus is disclosed in JP 2001-216515A. The apparatus divides an input image into sub-regions to detect a candidate region for eyes and a candidate region for an area between the eyes by utilizing the luminance feature of each sub-region. Then, the area between the eyes is determined by the positional relationship of the candidate region for the eyes and the candidate region for the area between the eyes to determine the face and eye regions so as to include the detected region of the area between the eyes.

However, the face detection apparatus disclosed in JP 2001-216515A detects a narrow region such as the area between the eyes in a wide face region, therefore leading to a large load imposed during the image processing. Further, the apparatus judges whether a subject wears a pair of glasses based on a gray level histogram or edge information of the sub regions which are adjacent vertically and horizontally. Thus, the determination of the presence of the glasses may be subject to influences of the frame design of the glasses. Since the apparatus identifies the positions of the left and right eyes based on the region of the area between the eyes, which is detected under the above-described conditions, the possibility of the error detection is not eliminated.

Further, an open and closed state detection apparatus is disclosed in JP 2004-220080A. The apparatus detects the open and closed state of a driver's eye who operates a movable body such as a vehicle. The open and closed state detection apparatus disclosed in JP 2004-220080A captures an image of a subject's face to detect an (image of) upper eyelid in the obtained face image, and then the apparatus approximates the detected eyelid by a multidimensional curve to calculate the curvature of the approximated multidimensional curve. The calculated curvature is set as a curvature of the upper eyelid, and the state of the eye is judged to be open or closed based on how large (or small) the curvature is.

In the above-described open and closed detection technology, when detecting the upper eyelid in the face image, the error detection of the upper eyelid may occur due to influence of ambient light and the glasses. In addition, it is necessary to approximate the eyelid by the multidimensional curve and calculate the curvature of the approximated multidimensional curve in each upper eyelid detection process. Hence, an enormous amount of processing operation is required.

A need exists for an eyelid detection apparatus which is not susceptible to the drawback mentioned above.

SUMMARY OF THE INVENTION

According to an aspect of the present invention, an eyelid detection apparatus includes a face image storing process storing a plurality of face images of a subject captured at different timings, a change detecting process detecting changes in each face image caused by blinking after processing the plurality of face images stored by the face image storing process, and an eyelid detecting process detecting a position of an eyelid of the subject based on the changes detected by the change detecting process.

According to a second aspect of the present invention, an eyelid detection apparatus includes a face image storing process storing face images of a subject, an edge line extracting process extracting edge lines from a predetermined region of each face image stored by the face image storing process based on a gray level of the image, an eyelid candidate extracting process extracting edge line pairs, which are candidates for a combination of edge lines corresponding to upper and lower eyelids, from the edge lines extracted by the edge line extracting process, a centerline detecting process detecting a centerline of a face contour included in each image stored by the face image storing process, and an eyelid identifying process detecting the edge line pairs extracted by the eyelid candidate extracting process, each of the edge line pairs being paired with another edge line pair asymmetrically arranged with respect to the centerline detected by the centerline detecting process, and identifying the detected edge line pairs as the combination of the edge lines corresponding to the upper and lower eyelids of the subject.

According to a third aspect of the present invention, a program instructs a computer to function as a face image storing process storing a plurality of face images of a subject captured at different timings, an edge line extracting process extracting edge lines, each corresponding to a boundary of each image region, after processing the face images stored by the face image storing process, an eyelid candidate extracting process extracting edge line pairs, which are candidates for a combination of edge lines corresponding to upper and lower eyelids, from the edge lines extracted by the edge line extracting process, an eyelid identifying process identifying an edge line pair having an upper eyelid candidate edge line whose representative point moves in a predetermined direction as the edge line pair corresponding to the upper and lower eyelids of the subject, from the edge line pairs extracted by the eyelid candidate extracting process.

According to a fourth aspect of the present invention, a program instructs the computer to function as an image storing process storing images including a face of a subject, a face region detecting process detecting a face region in each image stored by the image storing process, a normalization process normalizing the face regions detected by the face region detecting process to be a predetermined size and creating face region images, a face image storing process storing the face region images created by the normalization process, a difference image creating process creating difference images by taking differences between a latest face region image and other face region images accumulated by the face image storing process, an active region detecting process detecting regions, each having a gray level value higher than or equal to a predetermined value, as active regions in each of the difference images, a difference image selecting process selecting a difference image whose active region is detected as a largest active region by the active region detecting process in the difference images, and an eye region identifying process identifying an eye region from the active regions of the difference image selected by the difference image selecting process.

BRIEF DESCRIPTION OF THE DRAWINGS

The foregoing and additional features and characteristics of the present invention will become more apparent from the following detailed description considered with reference to the accompanying drawings, wherein:

FIGS. 14A to 14G are diagrams showing a specific example of the difference image creation;

FIGS. 15A and 15B are diagrams showing a specific example of the eye region detection;

FIGS. 16A and 16B are diagrams for outlining processing according to a third embodiment of the invention;

DETAILED DESCRIPTION

Hereinafter, an eyelid detection apparatus 50 according to a first embodiment of the invention will be described. The eyelid detection apparatus 50 detects changes caused by blinking in a plurality of face images of a driver, and further detects a position of an eyelid in the changed portion. The eyelid detection apparatus 50 according to the first embodiment extracts the edge lines of eyelid candidates by extracting edge lines based on a gray level of each image and identifies a combination of one edge line whose representative point (centroids are used as a representing point in this embodiment) moves in a predetermined direction and the other edge line whose representative point does not move as the eyelid.

Figure 1:
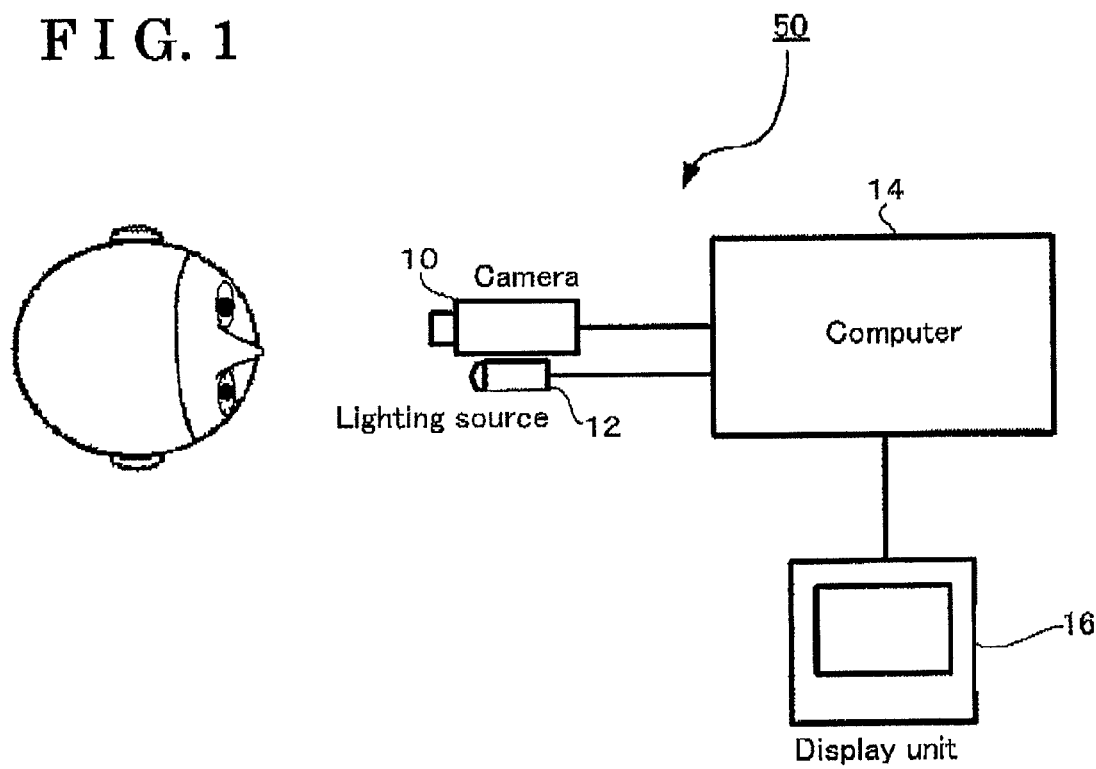
FIG. 1 is a block diagram showing a configuration of an eyelid detection apparatus according to a first embodiment of the invention.

As illustrated in FIG. 1 the eyelid detection apparatus 50 used in each embodiment of the invention is composed of a camera 10, a lighting source 12 lighting a driver's face, a computer 14 and a display unit 16 connected to the computer 14. The camera 10 captures images of the driver's face to create the face images and the computer 14 detects a center position of the driver's face.

The camera 10, composed of a CCD camera and the like, captures gray-scale images of the driver's face at a predetermined cycle (for instance, 1/30 seconds) to output the images. The face images sequentially output from the camera 10 include not only the images of the driver's face, but also the images of the background.

The display unit 16, composed of a LCD (Liquid Crystal Display) or a CRT (Cathode Ray Tube), displays binarized images created based on the face images captured by the camera 10 and the like. The display 16 is not an essential component in the apparatus, and may be eliminated therefrom.

Figure 2:
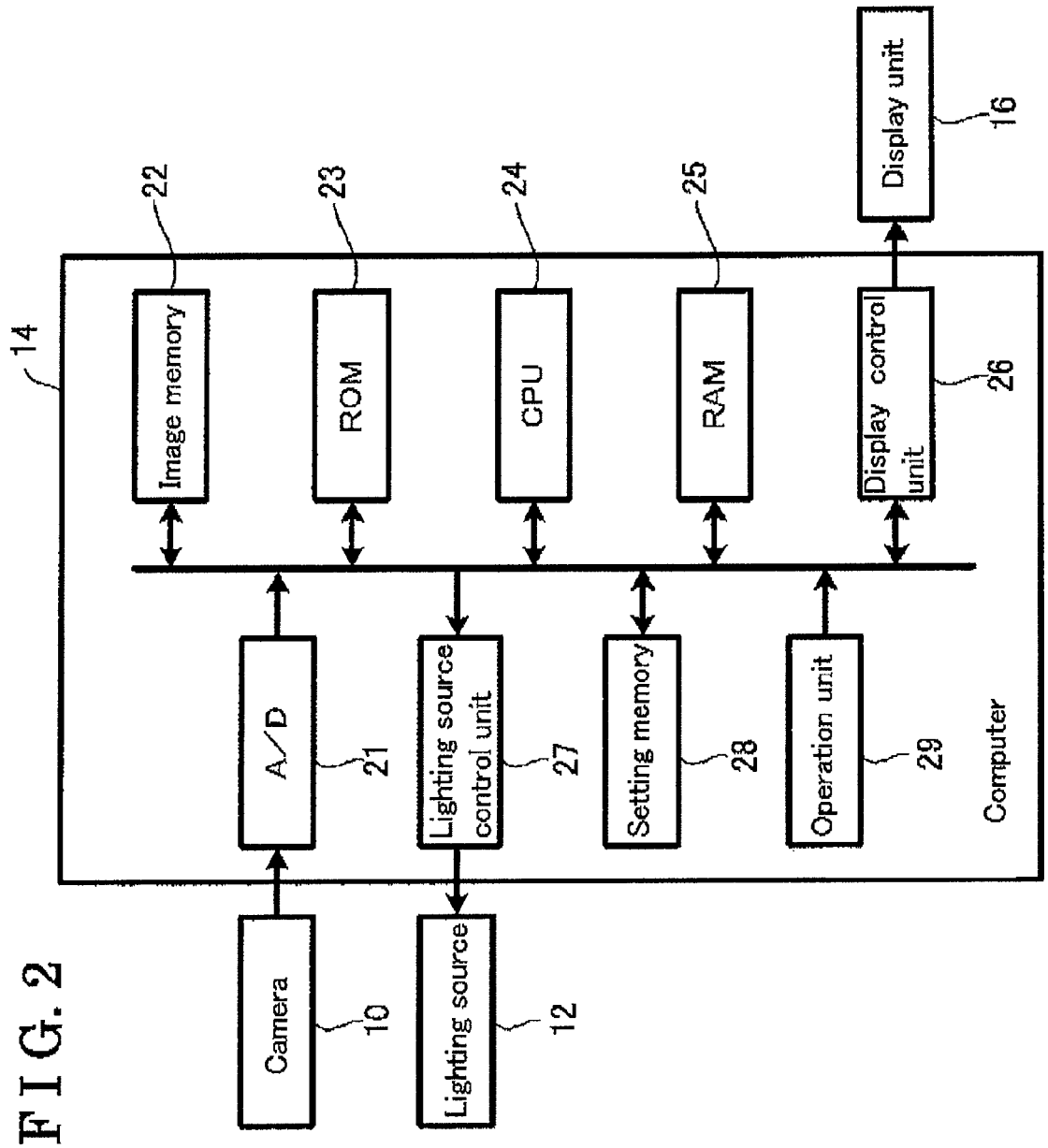
FIG. 2 is a block diagram showing a configuration of a computer shown in FIG. 1.

The computer 14 processes the face motion images captured by the camera 10 to detect the position of the eyelid. As shown in FIG. 2, the computer 14 is composed of an A-D converter 21, an image memory 22, a ROM (Read Only Memory) 23, a CPU (Central Processing Unit) 24, a RAM (Random Access Memory) 25, a display control unit 26, a lighting source control unit 27, a setting memory 28, and an operation unit 29.

The A-D (analog-digital) converter 21 converts an analog image signal captured by the camera 10 into a digital signal.

The image memory 22 is created by the camera 10 to store image data which are digitized by the A-D converter 21.

The ROM 23 stores programs for controlling the CPU operation. Further, the ROM 23 stores various kinds of fixed data used for executing image processing described below.

The CPU 24 controls the computer 14 entirely. Further, the CPU 24 executes the programs stored in the ROM 23 to process the succession of the face images captured by the camera 10 and to detect the eyelid. The RAM 25 functions as a work area of the CPU 24.

The display control unit 26 converts the image data and the like into the data format so as to be output by the display unit 16 and outputs the converted data on the display unit 16 under the control of the CPU 24.

The lighting source control unit 27 controls the turning on and off of the lighting source 12.

The setting memory 28 stores information (hereinafter, referred to as setting information) regarding the setting of the processing executed when the CPU 24 processes the face motion images to detect the eyelid.

The operation unit 29 receives operation information from a user and sends an operation signal suitable for each operation to the CPU 24.

Figures 3A, 3B, 3C:
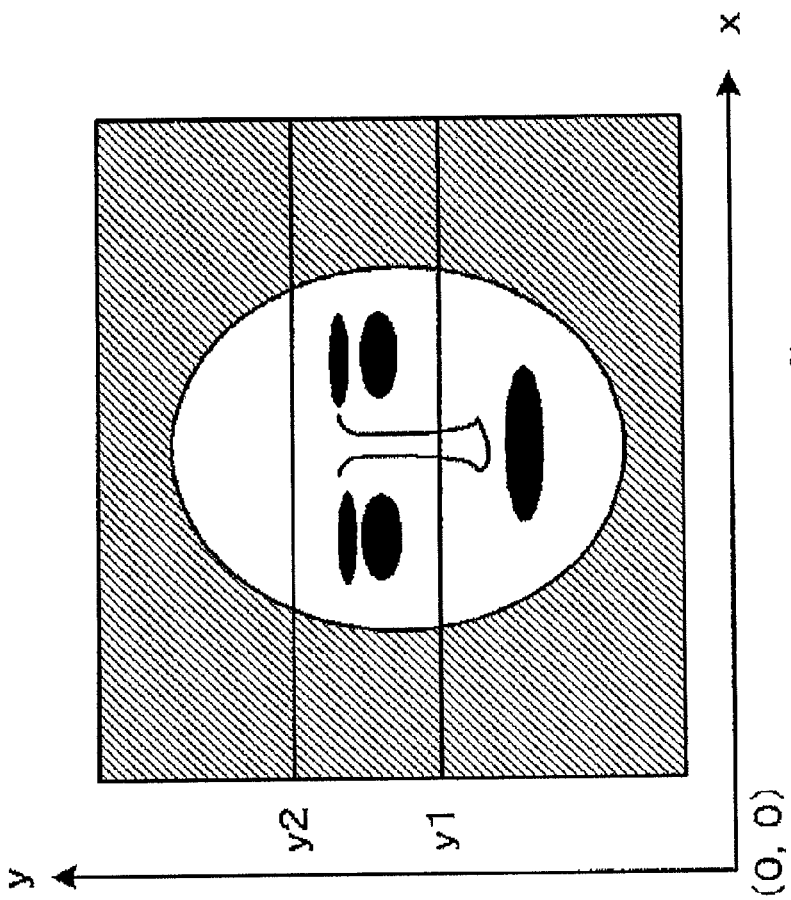
FIGS. 3A to 3C are diagrams used for describing various kinds of data stored in a ROM or a RAM.

Next, an example of the fixed data stoked in the ROM 23 will be described with reference to FIGS. 3A, 3B and 3C. Firstly, as shown in FIG. 3A, the ROM 23 stores an operator of a sobel filter for the transverse edge lines. The sobel filter for the transverse edge lines is an operator for stressing gray level differences appeared in a transverse direction, as shown in FIG. 3B.

The setting memory 28 pre-stores the setting information indicating regions where images of the eyes and the eyebrows are presumed to be present in the face images stored in the RAM 25, as shown in FIG. 3C. For example, in FIG. 3C, the region where the images of the eyes and the eyebrows are presumed to be present is set so as to be within a range in which a value of the y-axis is larger than y1 and smaller than y2 ($y1 \leq y \leq y2$). Hereinafter, the region where the images of the eyes and the eyebrows are presumed to be present is referred to as a setting region.

Hereinafter, an operation of the eyelid detection apparatus 50 according to the first embodiment will be described. In the first embodiment, the eyelid detecting apparatus 50 is configured as described above.

Firstly, an operation of the eyelid detecting apparatus 50 for detecting the eyelid in the face image will be outlined with reference to FIG. 4.

The camera 10 captures face images of a subject as shown in FIG. 3C, at a predetermined cycle (for example, 1/30 seconds) to output the face images. The output face images are sequentially stored in the image memory 22. Then, the CPU 24 sequentially loads the face images stored in the image memory 22 to execute the following processing.

Figure 4A:
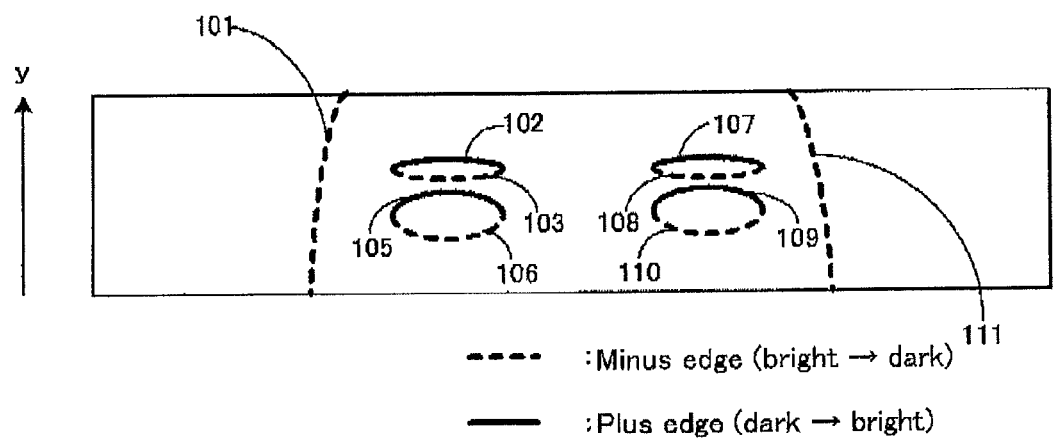
FIGS. 4A to 4C are diagrams used for outlining processing according to the first embodiment of the invention.

The CPU 24 obtains the setting region indicated by the setting information stored in the setting memory 28 and extracts transverse edge lines in the setting region of each face motion image by applying the sobel filter for the transverse edge lines shown in FIG. 3A. Consequently, as shown in FIG. 4A, edge lines whose pixels changes from a bright side to a dark side with respect to a y-axis are represented as minus edges and edge lines whose luminance changes from dark pixels to bright pixels with respect to the y-axis are represented as plus edges. In the drawings, the minus edges are indicated by a broken line and the plus edges are indicated by a solid line.

Next, the CPU 24 extracts combinations of the minus and plus edges, which satisfy the following three formulas, from among the minus and plus edge lines obtained in the previous processing.

$$Lp - Lm < Lth \quad (1)$$

Provided that Lp is a value indicating length of the plus edge, Lm is a value indicating length of the minus edge, and Lth indicates a threshold value. When formula (1) is satisfied, the lengths of the plus and minus edges are approximate within the threshold value Lth.

$$Cxp - Cxm < Cxth \quad (2)$$

Provided that Cxp indicates an x-coordinate of the centroid (representative point) of the plus edge, Cxm indicates an x-coordinate of the centroid (representative point) of the minus edge, and Cxth indicate a threshold value. When the formula (2) is satisfied, the x-coordinates of the centroids of the plus and minus edges are approximate within the threshold value Cxth.

$$Dg < Dth \quad (3)$$

Provided that Dg indicates a distance between the centroids of the plus edge and the minus edge, and Dth indicates a threshold value. When the formula (3) is satisfied, an inter-centroid distance of the plus edge and the minus edge is below the threshold value Dth.

The CPU 24 extracts the combinations of the minus and plus edges by using the above-described three formulas. In the combinations, the plus edges are considered as upper eyelid candidates and the minus edges are considered as lower eyelid candidates.

Namely, when the formulas (1) to (3) are satisfied, the plus and minus edges, forming each combination, are identical in length, approximate, and the centroids of the plus and minus edges have the identical x-axis.

Figure 4B:
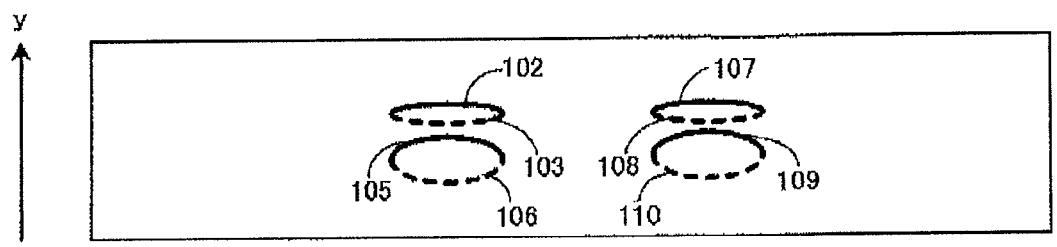

FIG. 4B shows an example of the combinations of the minus and plus edges extracted by using the formulas (1) to (3). The combinations of a plus edge 102 and a minus edge 103, of a plus edge 105 and a minus edge 106, of a plus edge 107 and a minus edge 108, and of a plus edge 109 and a minus edge 110 are the subject's eyelid candidates.

The CPU 24 analyzes the plurality of face images which are obtained at different tunings to determine which candidate, from among the above-described candidates, corresponds to the eyelid. Specifically, as described in FIG. 4C, when the centroid of the plus edge moves in a direction that the value of the y-axis increases (hereinafter, referred to as y-axis direction) or in a direction opposite to the y-axis direction and the centroid of the minus edge does not move much, the combination of the plus edge and the minus edge is identified as the eyelid. Here, the centroid is employed as the representative point of the edge line, however, other points may be employed as the representative point. For example, a point calculated by weighting edge strength, a local maximum point of the edge strength, a local minimum point of the edge strength, a highest point of the edge line in a longitudinal direction of the image, a lowest point of the edge line in the longitudinal direction of the image and the like may be employed as the representative point.

Here, eyelid detection processing executed by the eyelid detection apparatus 50 according to the first embodiment of the invention will be described in detail with reference to FIG. 5.

Figure 5:
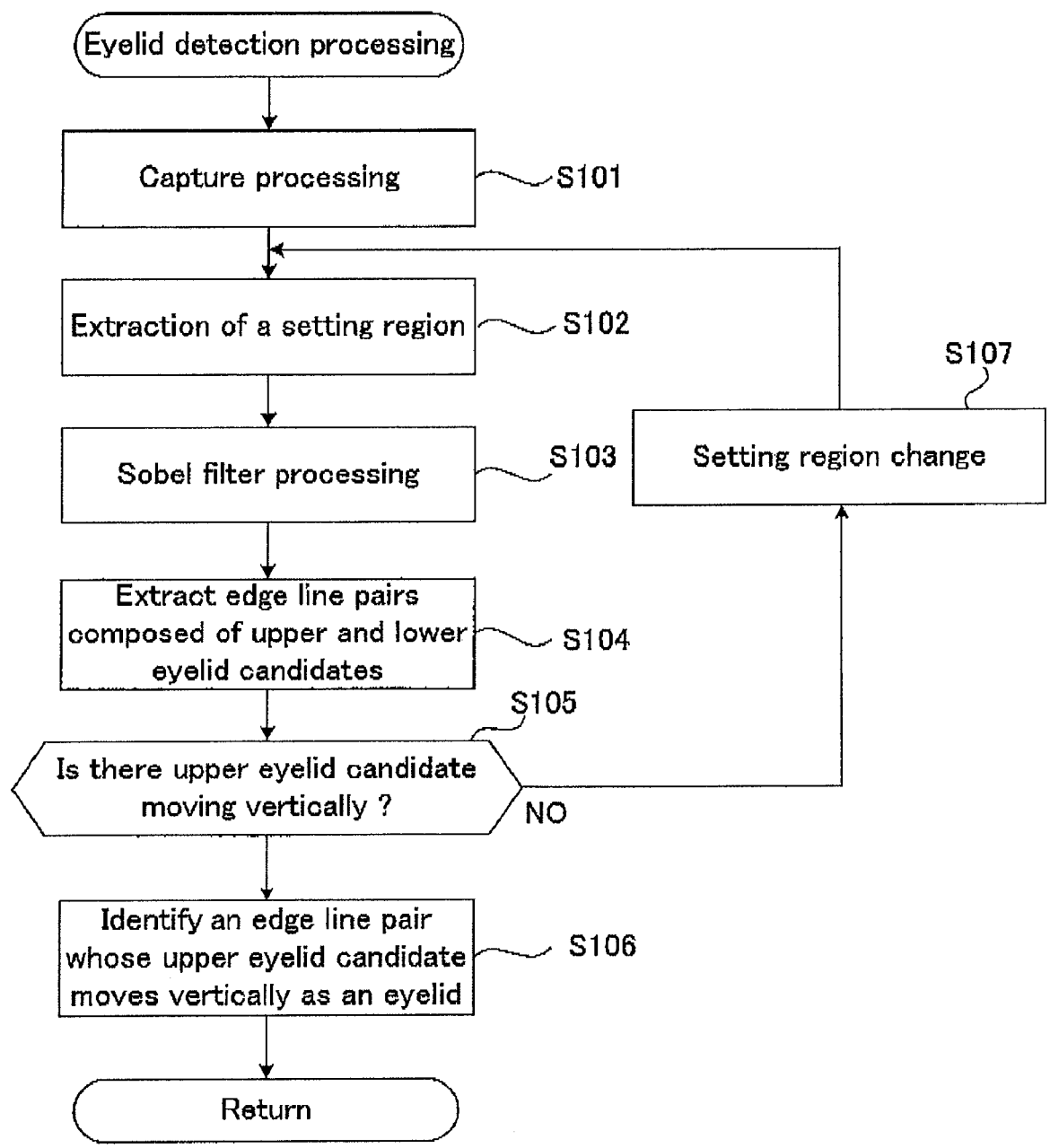
FIG. 5 is a flowchart used for describing eyelid detection processing of the first embodiment.

The CPU 24 initiates the processing of FIG. 5 at the predetermined cycle (for example, 1/30 seconds). The CPU 24 loads the subject's face images captured by the camera 10 via the A/D converter 21 to store the face images in the image memory 22 (Step S101) (face image storing means).

The CPU 24 extracts the setting region determined based on the setting information stored in the setting memory 28 from each face image stored in the image memory 22 (Step S102).

The CPU 24 extracts the transverse edge lines from the setting region of each face motion image by applying the sobel filter for the transverse edge lines stored in the ROM 23 (Step S103) (edge line extracting means).

The CPU 24 further extracts the combinations of the minus and plus edges, which satisfy the above-described formulas (1) to (3), from among the edge lines extracted in the previous step (Step S104) (eyelid candidate extracting means).

Figure 4C:
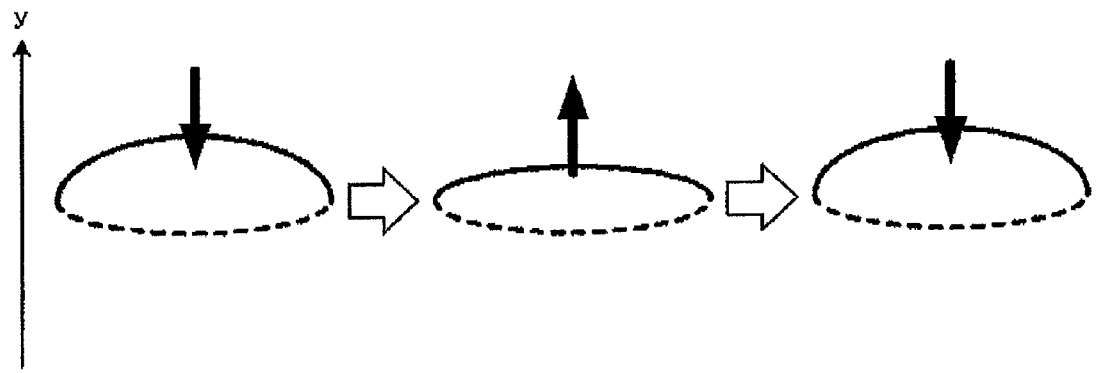

The CPU 24 respectively calculates the centroids of the plus and minus edges. Then, the CPU 24 further calculates the centroids of the pair of the plus and minus edges obtained from the previous face images to create a record of the centroids of each edge line obtained from the succession of the face images (change detecting means). The CPU 24 determines whether the combination of the plus edge whose centroid moves in the y-axis direction or the direction opposite to the y-axis direction as shown in FIG. 4C and the minus edge whose centroid does not move (much) is included in the extracted combinations (Step S105) (eyelid detecting means).

If no combination of the plus edge whose centroid moves in the y-axis direction or in the direction opposite to the y-axis direction and the minus edge whose centroid does not move is included (Step S105; NO), the CPU 24 changes the setting information stored in the setting memory 28 to change or expand the setting region (Step S107) and then the processing is resumed from Step S102.

If the combination of the plus edge whose centroid moves in the y-axis direction or in the direction opposite to the y-axis direction and the minus edge whose centroid does not move is included (Step S105; YES), the CPU 24 identities the combination of the plus and minus edges as the eyelid of the subject (Step S106) (eyelid identifying means) and terminates the processing.

In this way, the eyelid detection apparatus 50 according to the first embodiment of the invention correctly detects the eyelid, i.e. the position of the eye, with fewer processing operations.

The positions of the upper and lower eyelids are identified as described above, and the information is utilized for identifying a driver's gaze direction, and determining whether or not the driver is awake. For instance, a position of a pupil corresponding to the position of the eyelid is determined as well as face orientation, and the driver's gaze direction is determined based on the information. The information indicative of the driver's gaze direction may be utilized for various kinds of vehicle control. Further, when a state, in which a distance between the upper and lower eyelids is shorter than a certain criteria, lasts for a predefined period, it is assumed that the driver falls asleep, and predetermined controls may be performed.

Second embodiment will be described as follows.

In the first embodiment, the eyelid detection apparatus 50 identifies the combination(s) of the plus edge whose centroid moves in the predetermined directions and the minus edge whose centroid does not move (much) as the subject's eyelid(s) from the extracted combination of the minus and plus edges. In the second embodiment, differences between the images are taken to extract changed portions of the images. Then, the apparatus detects the eyelid in the changed portions. Namely, the eyelid detection apparatus 50 detects blinking of the driver, thereby detecting the positions of the eyelids (eye region).

The operation of the eyelid detection apparatus 50, detecting an eye region in each face image, will be described.

Figure 6:
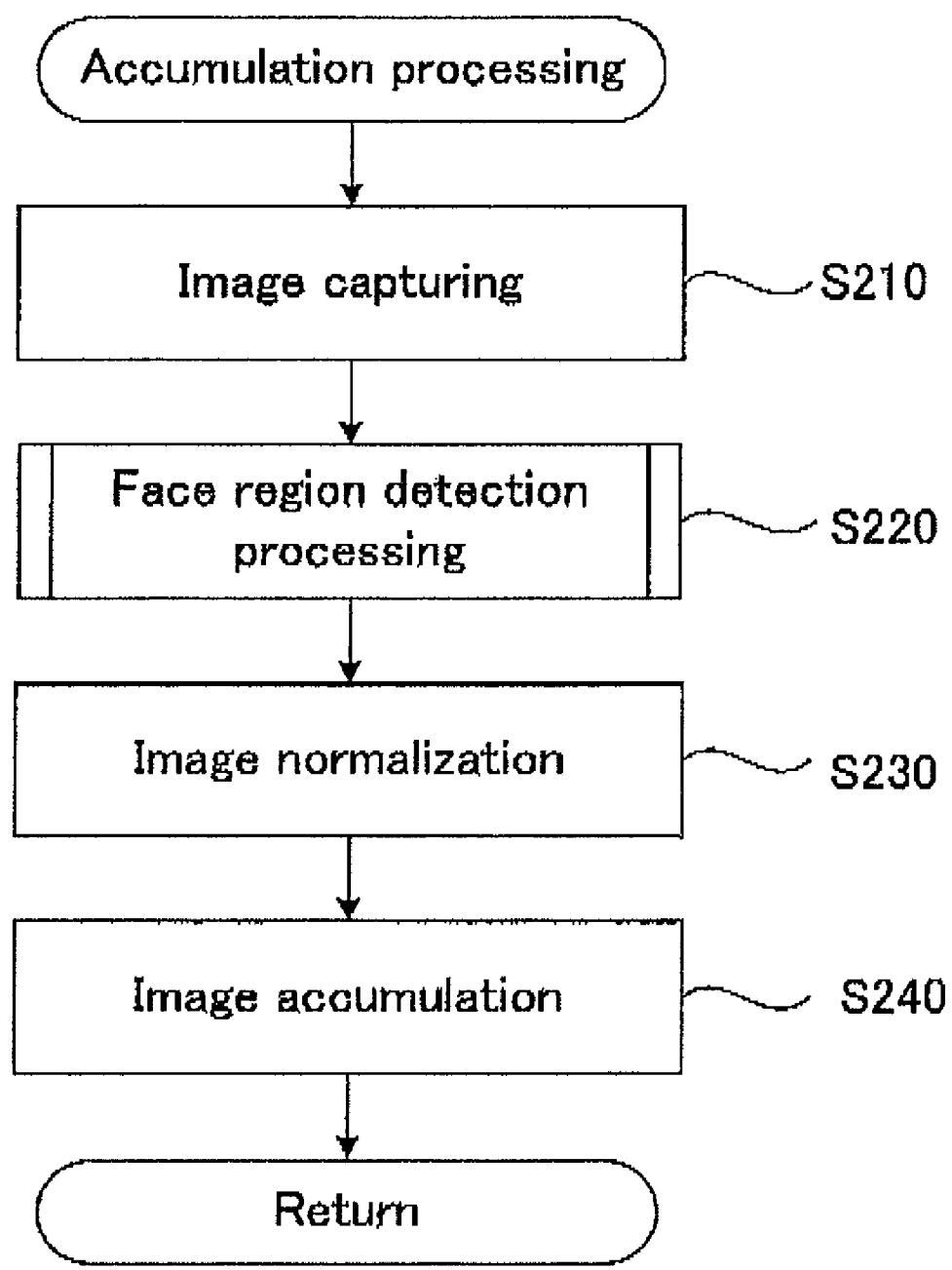
FIG. 6 is a flowchart showing an operation of accumulating processing of an eyelid detection apparatus according to a second embodiment of the invention.

FIG. 6 is a flowchart showing an operation of accumulation processing performed by the CPU 24. In the accumulation processing, the CPU 24 extracts a face region from each image captured by the camera 10 and accumulates the extracted data in the image memory 22 after normalization.

The CPU 24 executes the accumulating processing at a predetermined frame cycle, for example, 33 milliseconds (image storing means). First, the CPU 24 controls the camera 10 so as to capture the images (Step S210).

Next, the CPU 24 executes face region detection processing (Step S220). In the face region detection processing, the face region is detected in each original image including the face image, which is captured by the camera 10, for extraction.

Figure 7:
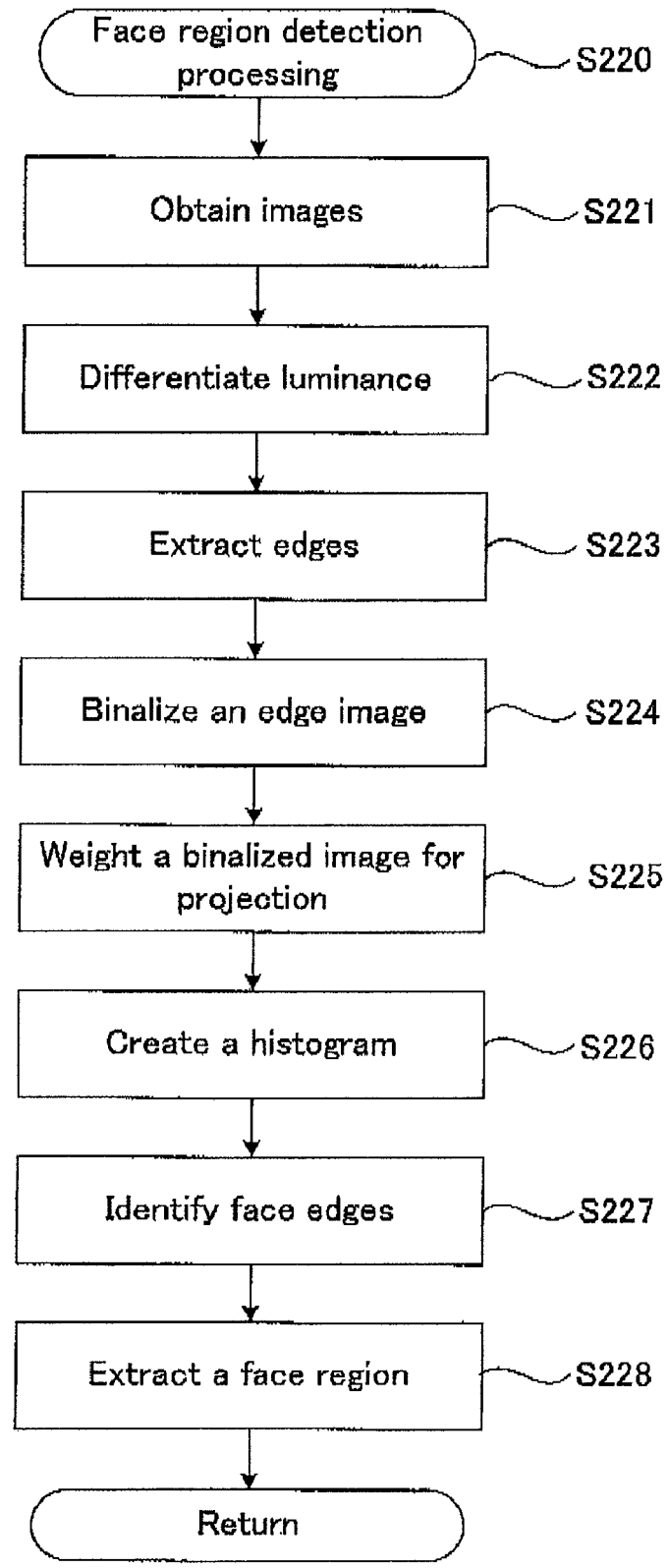
FIG. 7 is a flowchart showing an operation of face region detection processing shown in FIG. 6.

FIG. 7 is a flowchart showing an operation of the face region detection processing (Step S220). The CPU 24 obtains the images captured by the camera 10 (Step S221). Then, the CPU 24 differentiates luminance of each image with respect to a transverse direction of the image (Step S222) so as to extract a longitudinal edge image from each captured image (Step S223). Further, in order to define the longitudinal edge portions obtained in Step S223, the longitudinal edge image is binarized (Step S224). Subsequently, the binarized image is weighed by longitudinal length to be projected (Step S225) for creation of a histogram (Step S226). Specifically, the image is weighted by a square of the longitudinal length of the edge and is projected for stressing the longitudinally long edges. Steps 225 to 226 allow longitudinally long face edges to be identified (Step S227).

Transverse edges are obtained by repeating a similar processing. However, in this case, the processing is executed with respect to a longitudinal direction of the image (Step S221 to S227).

After obtaining the longitudinal and transverse edges by the processing executed from Step S 221 to S 227, a portion surrounded by both edges is extracted as the face region (Step S228) (face region detecting means).

As just described, the face region is detected and extracted in the face region detection processing. Meanwhile, the method detecting the face region from the image is not limited to the above-described method. For example, similarly to the first embodiment, the sobel filter may be applied. Alternatively, the face region may be detected by differentiating the accumulated captured images over time (taking differences) and creating a histogram based on the differentiated images. Further, the alternative method may be integrated with the above-described method. Furthermore, the face region may be detected by matching the image with a pre-registered template.

Next, the CPU 24 normalizes the face region images (Step S230). Here, normalization means converting the data into a desired form by following a certain rule for easy handling, and the face region extracted in the face region detection processing (Step S 220) is normalized to a predetermined size. The face region extracted in the face region detection processing constantly varies in size or form depending on posture of the driver and the like. In this processing, in order to perform inter-frame differentiation of the face region images, the size of the images is normalized for handling the images uniformly. Specifically, each face image extracted in the face region detection processing (Step S 220) is linearly normalized so as to be an image whose size is 100 pixels by 100 pixels (normalization means). Additionally, the CPU 24 stores parameters used for normalization in the RAM 25 so as to convert the eye region obtained from the normalized image into coordinate values of the original image (Step S230). Further, the gray level may be normalized.

Then, the CPU 24 stores the face images normalized in Step S230 in the image memory 22 (Step S240) (normalized image storing means). Since only the normalized face region images are accumulated here, the memory region of the image memory 22 is saved. In order to perform inter-frame differentiation, the plurality of the normalized face region images are required to be accumulated. In this processing, the face region images are accumulated for 150 milliseconds. This time period is longer than a time period corresponding to four frames and is determined based on a time period required for human to close his/her eye, which is estimated by statistical research.

Figure 13A:
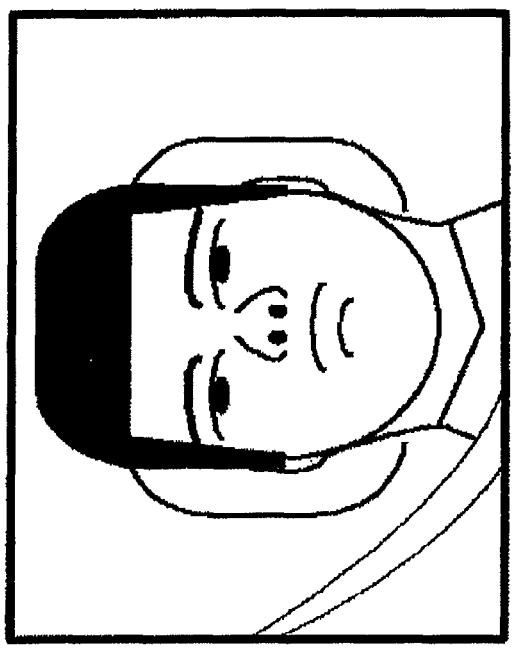
FIGS. 13A to 13C are diagrams showing a specific example of the face image detection.
Figure 13B:
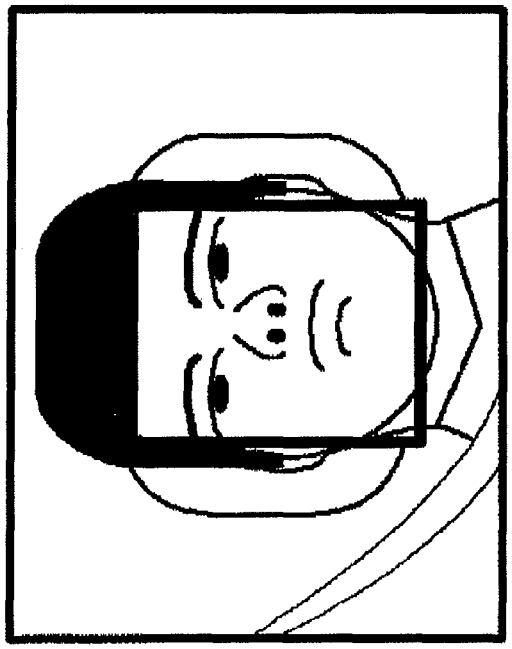
Figure 13C:

Specifically, assume that an image including a face of a driver, i.e. the original image shown in FIG. 13A in Step S210. A face region is detected as shown in FIG. 13B by the face region detection processing (Step S220). Then, as shown in FIG. 13C, the face image is normalized in Step S230.

Figure 8:
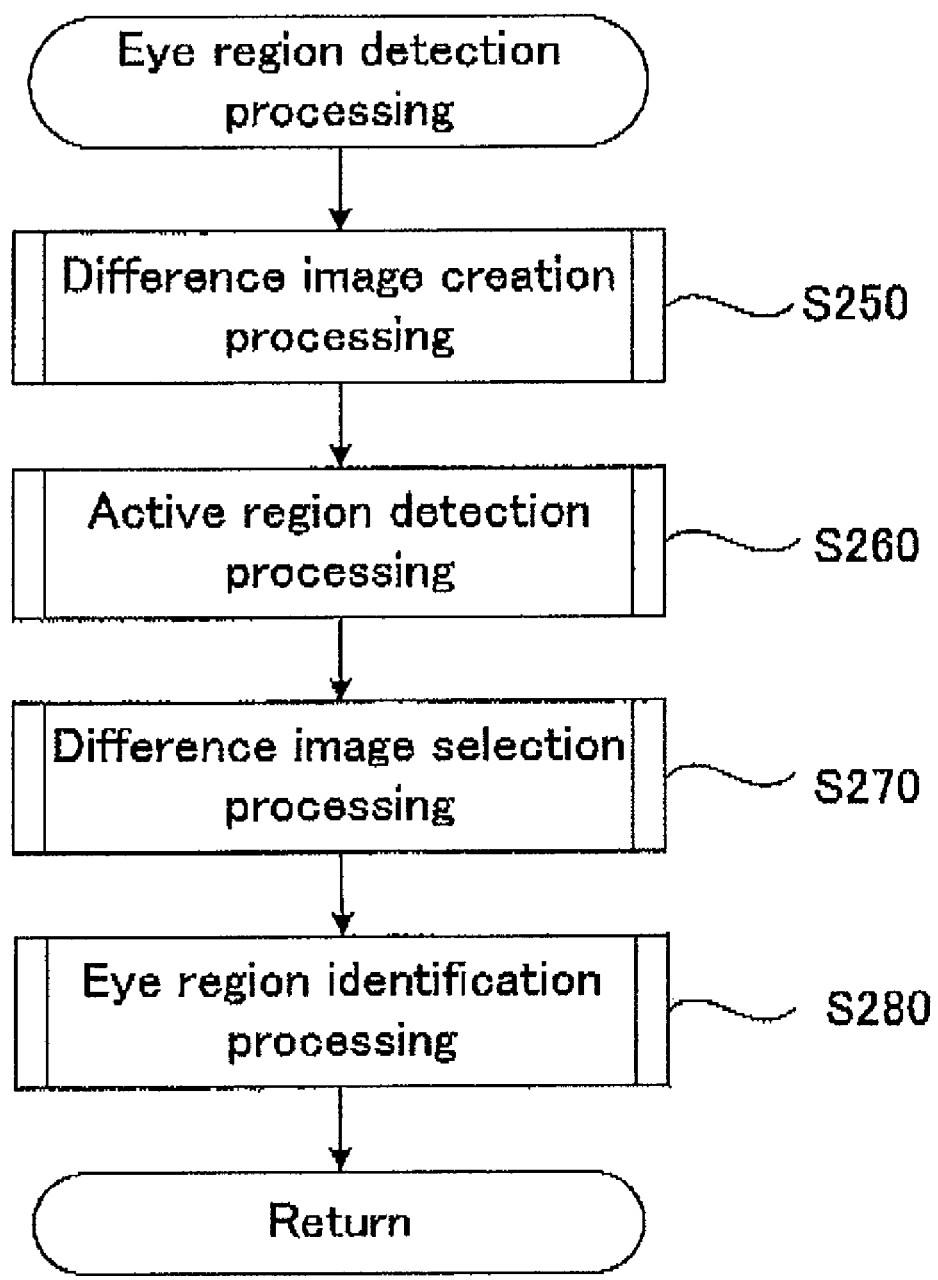
FIG. 8 is a flowchart used for describing an operation of eye region detection processing of the eyelid detection apparatus according to the second embodiment.

Next, eye region detection processing will be described. In the eye region detection processing, an eye region is detected in each face image accumulated in the image memory 22. FIG. 8 is a flowchart used for describing an operation of the eye region detection processing.

In the eye region detection processing, firstly, the CPU 24 executes difference image creation processing (Step S250). In the difference image creation processing, differences between the latest image and the other images, accumulated in the image memory 22, are taken to create difference images. Details of the processing will be described below.

Next, the CPU 24 executes active region detection processing (Step S260). In the active region detection processing, moving regions (active region) are detected based on the difference images created in the difference image creation processing (Step S250). Details of the processing will be described below.

Subsequently, the CPU 24 executes difference image selection processing (Step S270). In the difference image selection processing, a difference image, used for detecting the eye region, is selected from among the plurality of difference images whose active regions detected in the active region detection processing (Step S260) after being created in the difference image creation processing (Step S250). Details of the processing will be described below.

The CPU 24 executes eye region identification processing (Step S280). In the eye region identification processing, the eye region is identified from the active regions of the difference image selected in the difference image section processing (Step S270). Details of the processing will be described below.

Figure 9:
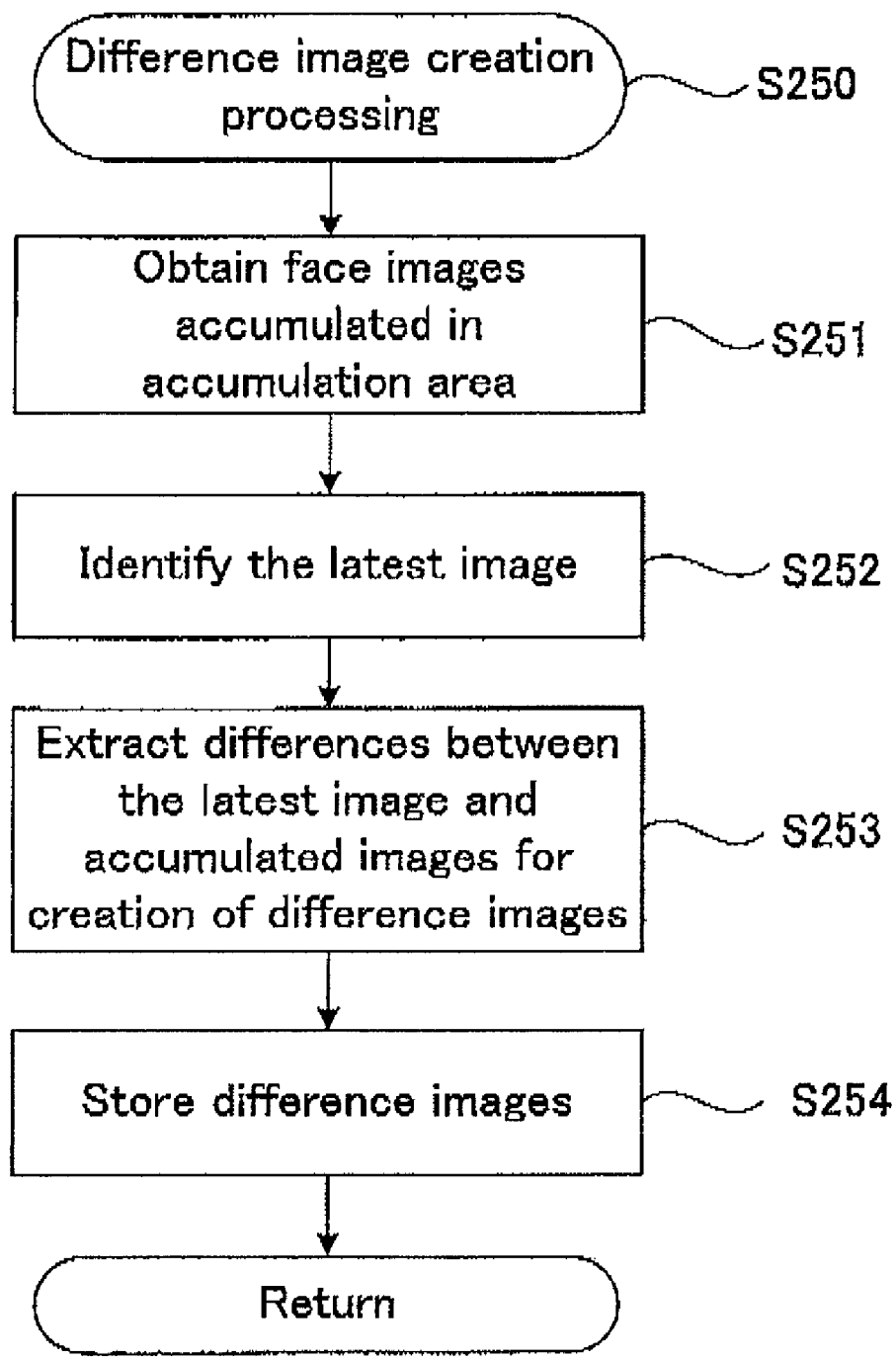
FIG. 9 is a flowchart showing an operation of difference image creation processing shown in FIG. 8.

Next, an operation of each step of the eye region detection processing will be described in detail. FIG. 9 is a flowchart showing the operation of the difference image creation processing (Step S250). In the difference image creation processing, the CPU 24 obtains the plurality of face images accumulated in the image memory 22 (Step S 251). Then, the latest image is identified from among the obtained images (Step S252). Subsequently, the CPU 24 takes the differences between the latest image and the other images to create the plurality of difference images (Step S253) (difference image creating means) and stores the difference images in the RAM 25 (Step S254).

Specifically, as shown in FIGS. 14A to 14G, difference images FIGS. 14E, 14F, 14G are respectively created by taking differences between a latest normalized image (FIG. 14A) and a normalized image accumulated 66 milliseconds before (FIG. 14B), between the latest normalized image (FIG. 14A) and a normalized image accumulated 99 milliseconds before (FIG. 14C) and between the normalized image (FIG. 14A) and a normalized image accumulated 132 milliseconds before (FIG. 14D).

The difference images may be created by taking differences between pre-stored images, created by analyses such as statistics, and the latest normalized image.

Figure 10:
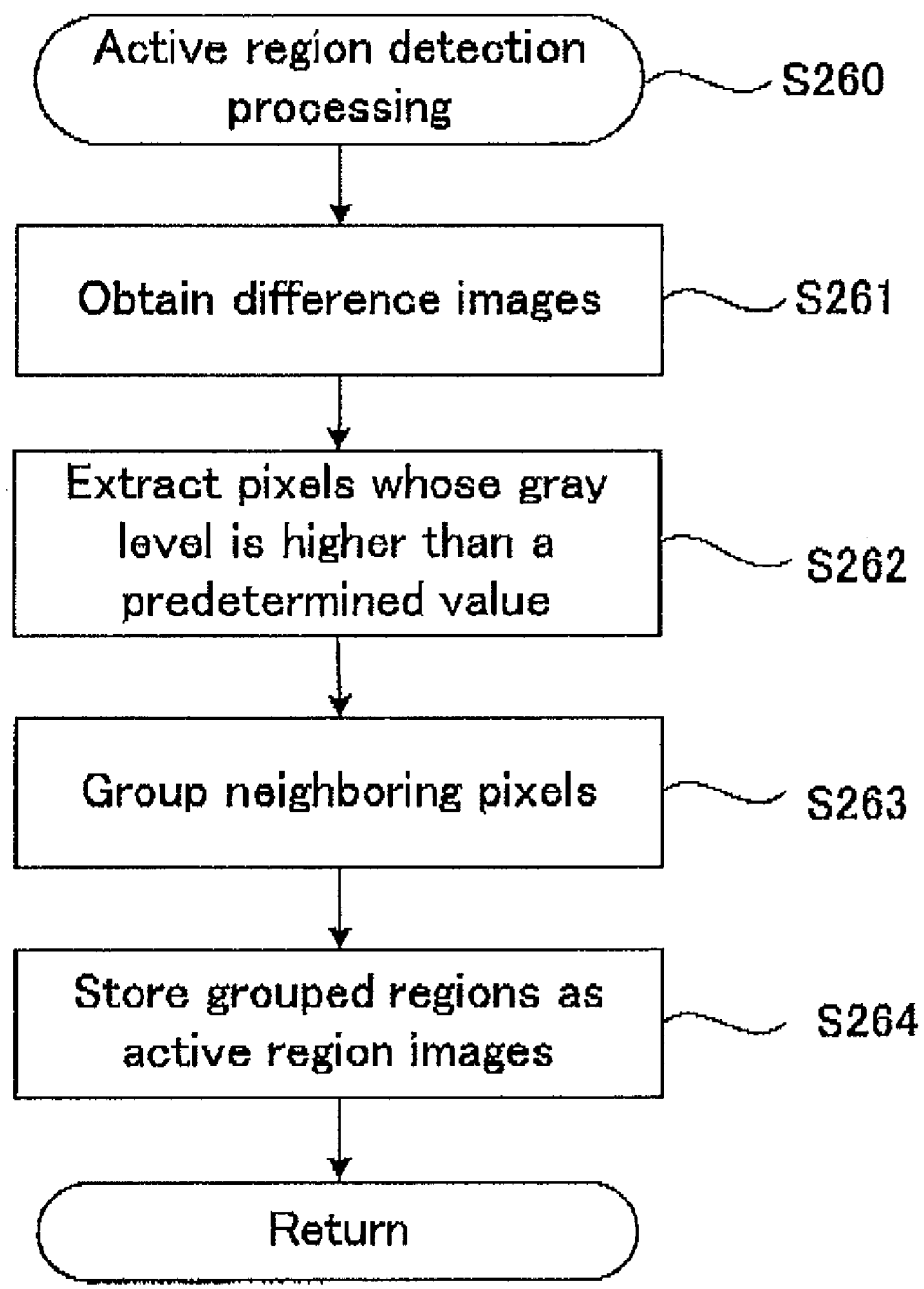
FIG. 10 is a flowchart showing an operation of active region detection processing shown in FIG. 8.

FIG. 10 is a flowchart showing the operation of the active region detection processing (Step S260). In the active region detection processing, firstly, the CPU 24 obtains the difference images created in the difference image creation processing (Step S250) in Step S261. Then, pixels having a gray level value larger than a predetermined value, for example, the pixels having the gray level value larger than or equal to 50 are extracted from the obtained difference images (Step S262). Then, the CPU 24 groups neighboring pixels extracted in Step S262 (Step S263). More specifically, the pixels located within 3 pixels are grouped together in this embodiment. The grouped regions are stored in the RAM 25 as an active region image (Step S264) (active region detecting means). These steps are iteratively looped back until the processing is completed for all of the difference images, thereby detecting the respective active regions in all of the difference images.

Meanwhile, resolution, gray-level contrast, and the like may be added to conditions used in the active region detection processing. Also, when grouping the pixels, the gray level information may be used for the grouping conditions as well as the pixel position information.

Figure 11:
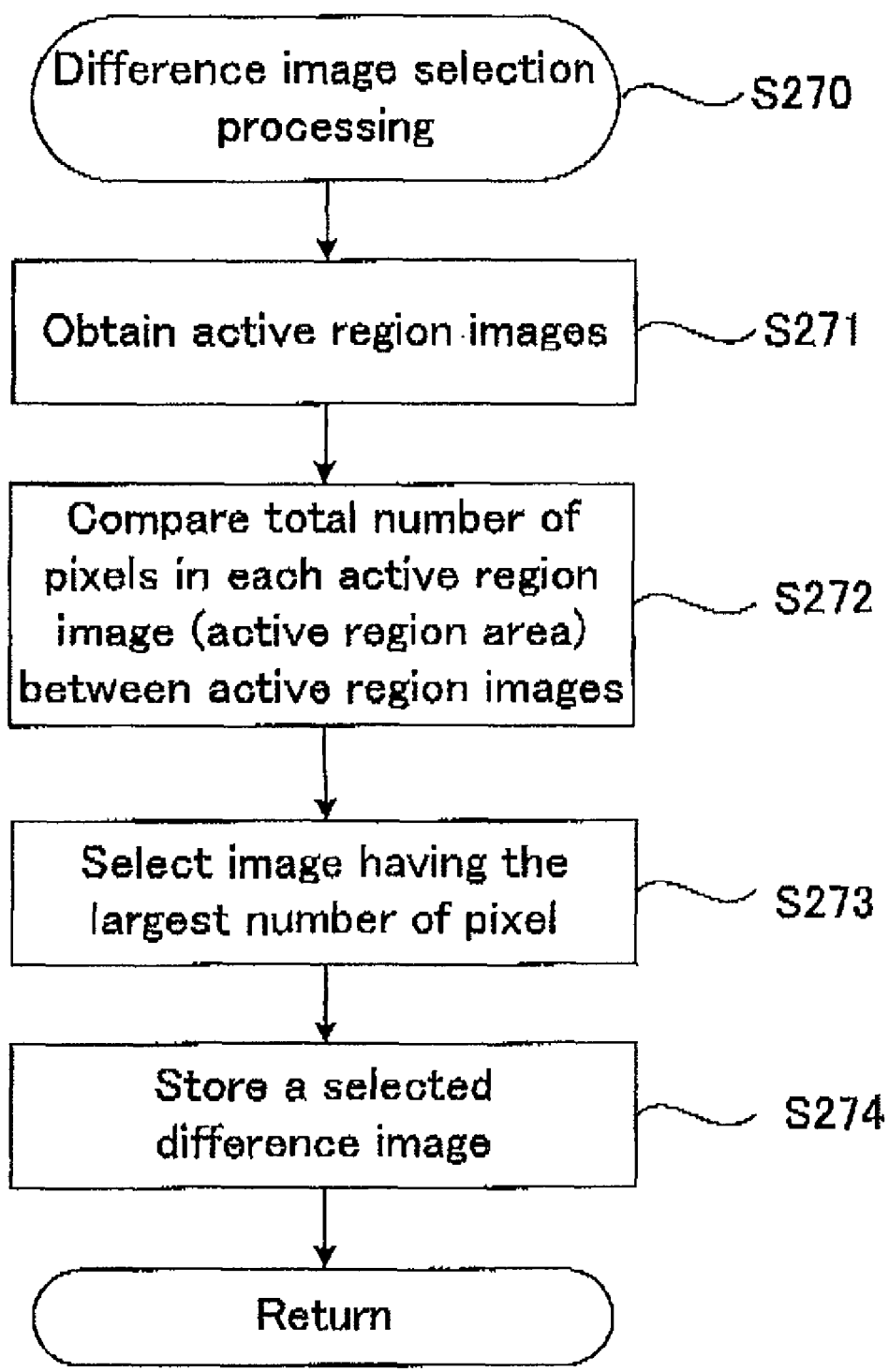
FIG. 11 is a flowchart showing an operation of difference image selection processing shown in FIG. 8.

FIG. 11 is a flowchart showing the operation of the difference image selection processing (Step S270). In the difference image selection processing, firstly, the CPU 24 obtains the plurality of difference images, i.e. active region image whose active region is detected in the active region detection processing (Step S260) in Step S271. Then, the CPU 24 compares the total number of pixels in the active regions, i.e. active region area between the difference images (Step S272). As a result of the comparison, the difference image having the largest number of the pixels (Step S273) is selected (difference image selecting means) to be stored in the RAM 25 (Step S274).

Specifically, FIG. 14F, having the largest active region area, is selected from among the difference images of FIGS. 14B to 14G.

As just described, the difference image is selected for the detection of the eye region. The difference image, having the largest active region in terms of area, is selected here, thereby selecting the difference image having the differences occurred between before and after the blinking of the driver.

Figure 12:
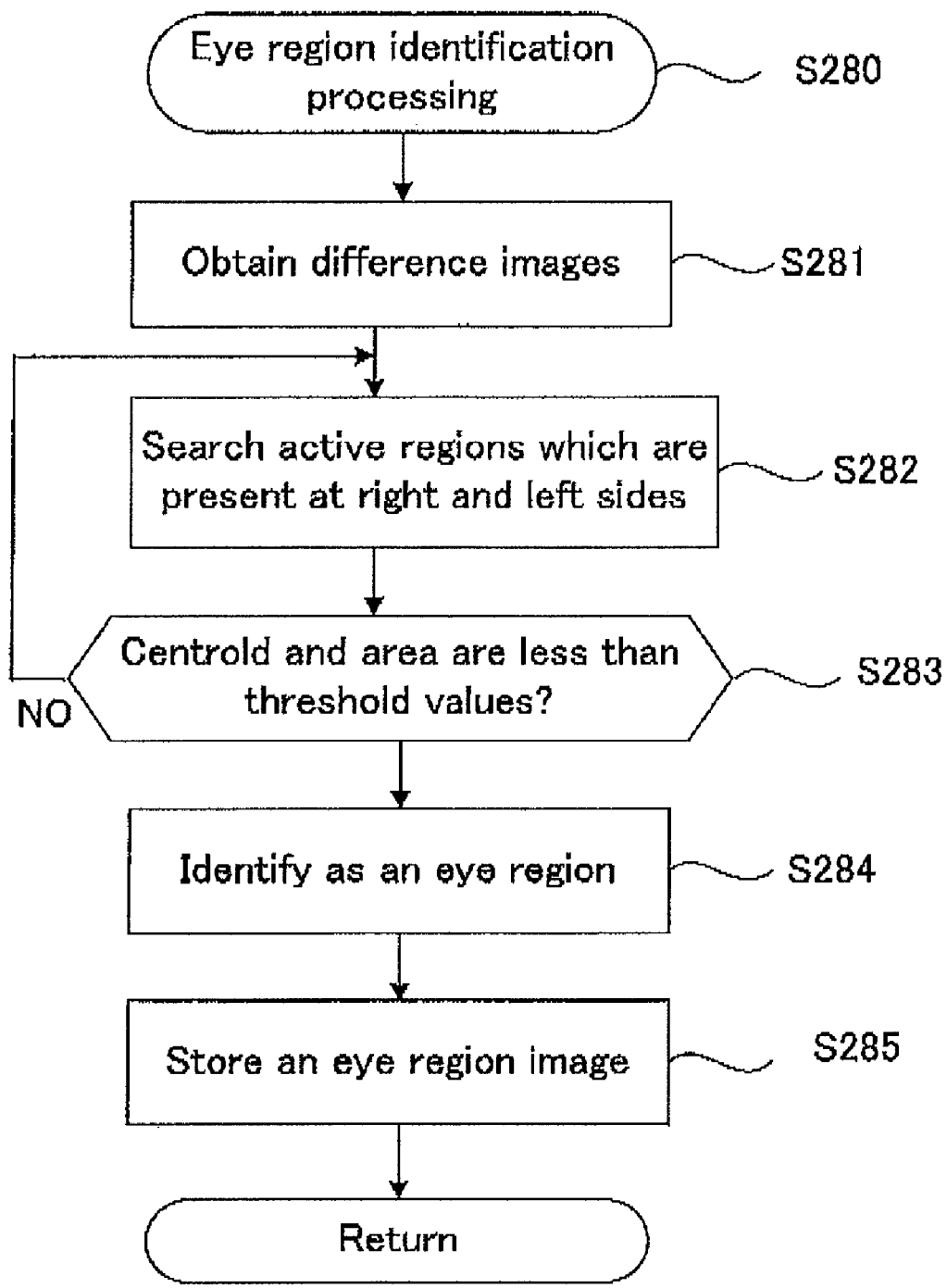
FIG. 12 is a flowchart showing an operation of eye region identification processing shown in FIG. 8.

FIG. 12 is a flowchart showing an operation of the eye region identification processing (Step S280). In the eye region identification processing, the eye region is identified by utilizing left-right symmetry of the eye region. In the eye region identification processing, the CPU 24 obtains the difference images selected in the difference image selection processing (Step S281). The CPU 24 then searches the active regions being present at left and right sides in the grouped active regions (Step S282) and determines whether or not centroid and area, i.e. the number of the pixels of each active region detected in Step S282 is with a predetermined threshold value (Step S283). If the centroid and the area are not within the threshold value (Step S283: NO), the processing returns to Step S282 in order to search the active region. Otherwise (Step S283; Yes), the active regions are identified as the eye region (Step S284) (eye region identifying means) so as to be stored in the RAM 25 (Step S285). Namely, in Steps 282 and 283, the active regions having the centroid and the area, which are unsuitable for the eye region, are excluded. For example, the active regions, which are ill-balanced, extremely small or left-right asymmetry, are excluded.

Specifically, a portion which is asymmetric in terms of area is excluded from the image shown in FIG. 15A and the eye region is identified as shown in FIG. 15B.

As just described above, the eye region is identified. In the eye region identification processing, in order to evaluate the left-right symmetry more accurately, a region having a high average value of the gray level, or a region having a peak of the gray level differences therein may be identified as the eye region. Further, positional relationship with the edge portion extracted from the original image may be added to the conditions for identification.

The image is converted into an original image size based on the parameter used for the normalization after the identification of the eye region. The converted image is used to identify the direction of the driver's gaze, and determine whether or not the driver is awake.

For example, the eye detection apparatus may detect the edge pair, as shown in the first embodiment in the region identified as the eye region and process one edge of the pair as an edge corresponding to the upper eyelid and the other edge of the pair as an edge corresponding to the lower eyelid.

In this case, whether the edge presumed to correspond to the upper eyelid is a real upper eyelid may be confirmed by checking movement of a centroid of the edge presumed to correspond to the upper eyelid. However, the confirmation is not an imperative procedure and may be omitted.

Further, the parameter of the eye may be extracted from the region identified as the eye region by any known methods for utilization in other controls.

As described above, the blinking of the eyes is extracted by taking the inter-frame difference. Thereafter, the eye is detected by utilizing pictorial features of the eye. Thus, the error detection of an eyebrow, a whisker, an eyeglass frame and the like is prevented. Further, the detection of the eye region is performed to a limited region, i.e. the face image, by utilizing the pictorial features of the eye and thus speeding up the processing time. The positions of the eyes are detected promptly with higher accuracy in this way.

Meanwhile, the subject of the normalization is not limited to the face size. For example, the gray level of the images (gray-scale) and colors may be normalized. In the case of the gray level normalization, for example, in order to uniform the average luminance of each image to be processed, the average luminance is determined for each image, and the ratio of the average luminance to the standard luminance, i.e. "the standard luminance/the average luminance" is obtained. Then, the luminance of each pixel is corrected by multiplying all pixels of each image by the above-mentioned ratio. Then, the accumulation processing is executed after the correction. Meanwhile, the standard luminance is a standard value common to the plurality of the images.

Third embodiment will be explained as follows.

In the first embodiment, the eyelid detection apparatus 50 identifies the combination of the plus edge whose centroid moves to the predetermined direction and the minus edge whose centroid does not move as the subject's eyelid from the extracted combinations of the minus and plus edges. In a third embodiment, a centerline of a contour of the subject's face is detected, and the combination of the minus and plus edges, which is axisymmetrically arranged to another combination of the minus and plus edges with respect to the centerline, is identified as the subject's eyelid. The configuration of the third embodiment is similar to that of the first embodiment.

Next an operation of the eyelid detection apparatus 50, detecting the eyelid in the face motion image, will be outlined with reference to FIGS. 16A and 16B.

Firstly, the eyelid detection apparatus 50 processes the face motion images in a similar manner to the first embodiment and obtains a centerline of a face contour from a face image shown in FIG. 16A.

Next, a setting region whose y-axis ranges from y1 to y2 is extracted from the image shown in FIG. 16A.

Then, the sobel filter is applied to each extracted image so as to extract a combination of plus and minus edges, as shown in FIG. 16B. Here, a combination of a plus edge 301 and a minus edge 302 is referred to as Candidate 1, a combination of a plus edge 305 and a minus edge 306 is referred to as Candidate 2, a combination of a plus edge 303 and a minus edge 304 is referred to as Candidate 3, a combination of a plus edge 307 and a minus edge 308 is referred to as Candidate 4, and a combination of a plus edge 309 and a minus edge 310 is referred to as Candidate 5.

The eyelid detection apparatus 50 excludes the candidate(s) that is (are) not paired with another edge line combination axisymmetrically arranged with respect to a centerline 200. Thus, Candidate 5, composed of the combination of the edge lines 309 and 310, is excluded. Subsequently, the combination, in which the centroid of the edge line corresponding to the upper eyelid moves, is selected from the remaining candidates. Namely, Candidates 3 and 4 are processed as the edge pair of the eyelid.

The eyelid detection processing executed by the eyelid detection apparatus 50 according to the third embodiment of the invention will be described in detail with reference to FIG. 17.

Figure 17:
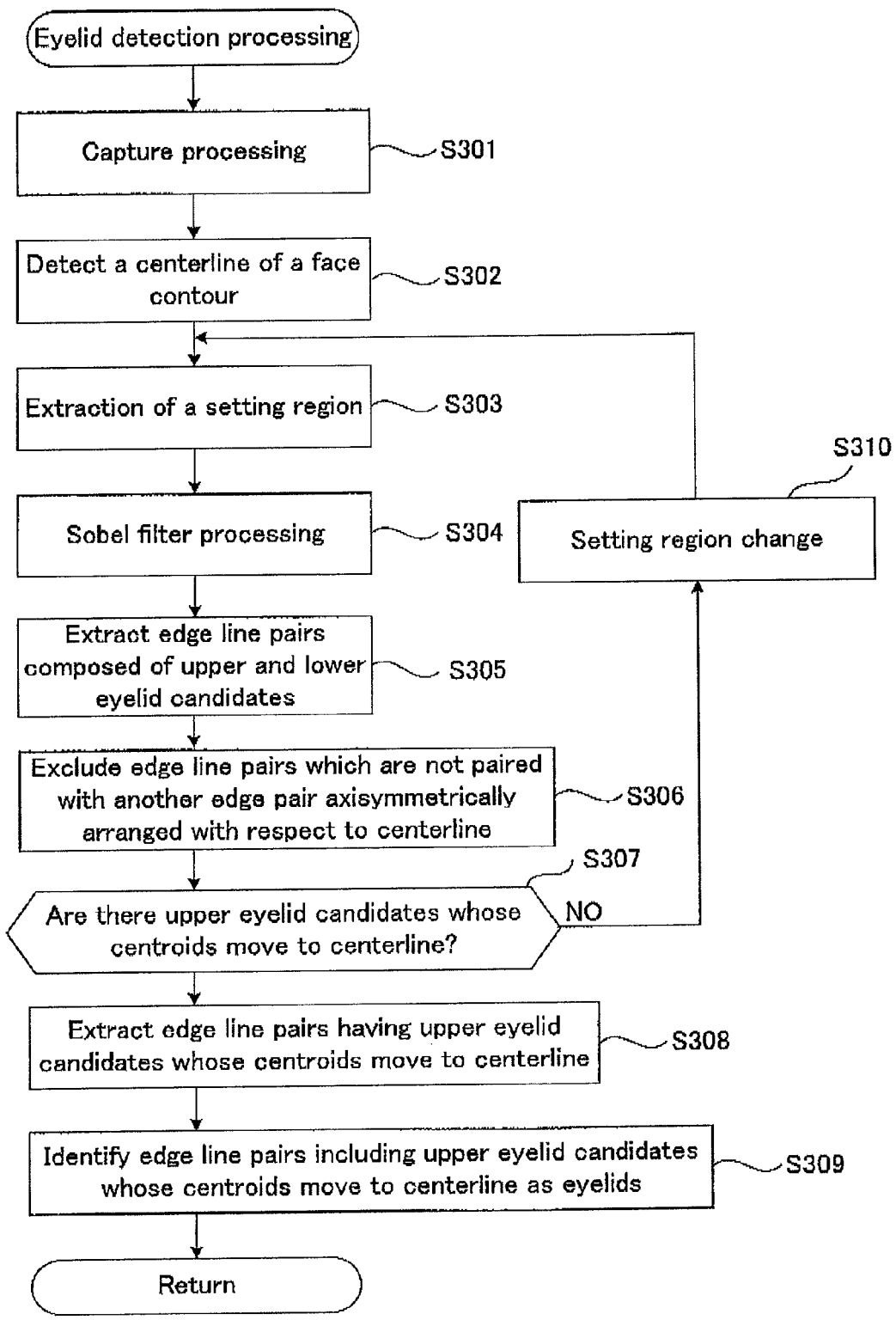
FIG. 17 is a flowchart used for describing eyelid detection processing of the third embodiment.

The CPU 24 initiates the processing of FIG. 17 periodically. Firstly, motion images of the subject's face are captured by the camera 10 via the A/D converter 21 to be stored in the image memory 22 (Step S301).

The CPU 24 detects the centerline of the face contour in each image which is obtained in Step S301 (Step S302) (centerline detecting means, detecting means).

The CPU 24 extracts the setting region determined based on the setting information stored in the setting memory 28 from each face image stored in the image memory 22 (Step S303).

The CPU 24 extracts the transverse edge lines from the setting region of each face image by applying the sobel filter for the transverse edge lines (Step S304).

The CPU 24 extracts the combinations of the minus and plus edges satisfying the formulas (1) to (3) used in the first embodiment from the extracted edge lines (Step S305).

The CPU 24 excludes the combination(s) that is (are) not paired with another edge line combination axisymmetrically arranged with respect to the centerline 200 from the combinations of the minus and plus edges extracted in Step S305 (Step S306) (eyelid candidate extracting means).

The CPU 24 determines whether or not the combination of the plus edge whose centroid moves to the centerline and the minus edge whose centroid does not move (much) is included in the remaining combinations of the plus and minus edges (Step S307).

When the combination of the plus edge whose centroid moves to the centerline and the minus edge whose centroid does not move (much) is not included in the remaining combinations (step S307; NO), the CPU24 changes the setting information stored in the setting memory 28 to change or expand the setting region (Step S310). Then, the processing returns to Step S303.

If the combination of the plus edge whose centroid moves to the centerline and the minus edge whose centroid does not move (much) is included in the remaining combinations (Step S307; YES), the CPU 24 extracts the combination of the minus and plus edges (Step S308).

The CPU 24 identifies the combination, which is paired with another combination axisymmetrically arranged with respect to the centerline 200 and composed of the plus edge whose centroid moves to the centerline and the minus edge whose centroid does not move (much), as the subject's eyelid (Step S309).

As just described, the eyelid detection apparatus 50 according to the third embodiment of the invention detects the eyelids correctly with fewer operations even when a subject's mouth and the like are included in the setting region.

In order to correspond to the first embodiment, a case that detects the eyelids is described as an example. However, the method adopted in the third embodiment may be applied to the identification of the eye region in Step S282 to S284, shown in FIG. 12 of the second embodiment.

A fourth embodiment will be described below.

In the first embodiment, the eyelid detection apparatus 50 identifies the combination of the plus edge whose centroid moves to the predetermined direction and the minus edge whose centroid does not move (much) as the subject's eyelid from the extracted combination of the minus and plus edges. In the fourth embodiment, whether or not blinking causes the centroid of the plus edge to move in the predetermined direction is confirmed. The combination of the minus and plus edges, in which a relationship between the movement of the centroid of the plus edge and the blinking is confined, is identified as the subject's eyelid. The configuration of the fourth embodiment is similar to that of the first embodiment.

Figure 18:
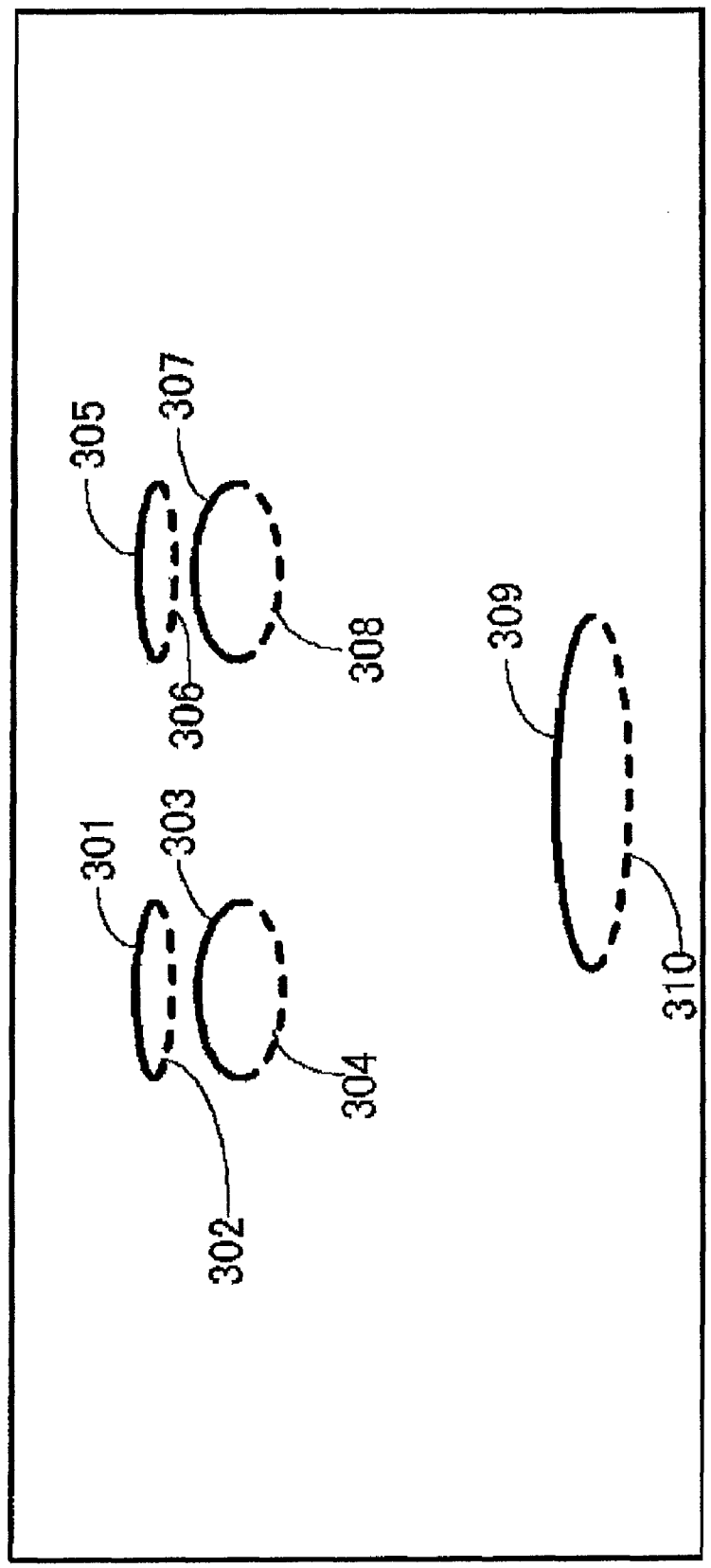
FIG. 18 is a diagram used for outlining processing according to a fourth embodiment of the invention.
Figure 19:
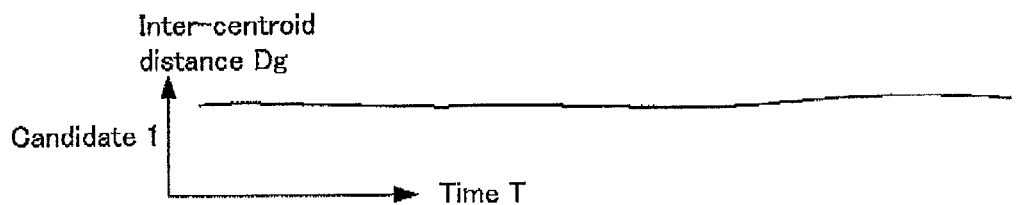
FIGS. 19A to 19E are diagrams used for outlining processing according to the fourth embodiment of the invention.
Figure 19:
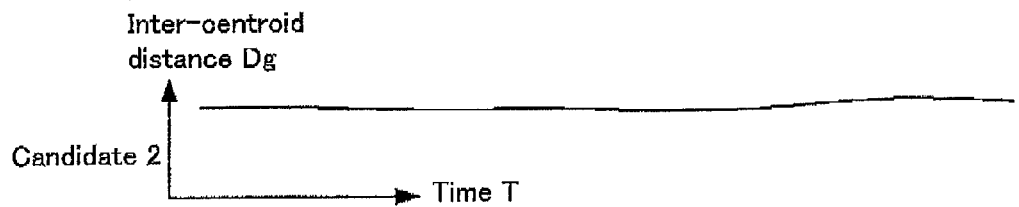
Figure 19:
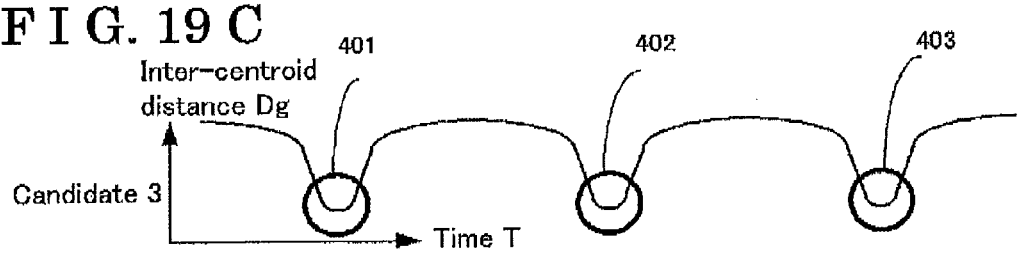
Figure 19:
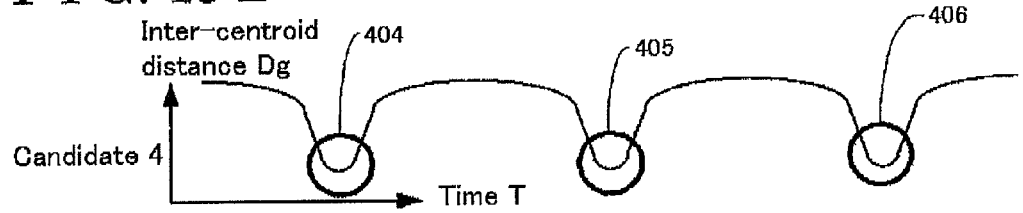
Figure 19:
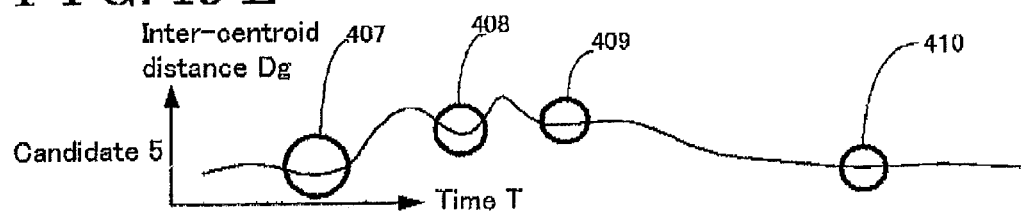

Next, an operation of the eyelid detection apparatus 50, detecting the eyelid in the face motion image, will be outlined with reference to FIGS. 18 and 19.

Firstly, the eyelid detection apparatus 50 processes the face motion images in the similar manner to the first embodiment and extracts the combinations of the minus and plus edges as shown in FIG. 18. Here, a combination of a plus edge 301 and a minus edge 302 is referred to as Candidate 1, a combination of a plus edge 305 and a minus edge 306 is referred to as Candidate 2, a combination of a plus edge 303 and a minus edge 304 is referred to as Candidate 3, a combination of a plus edge 307 and a minus edge 308 is referred to as Candidate 4, and a combination of a plus edge 309 and a minus edge 310 is referred to as Candidate 5.

The eyelid detection apparatus 50 monitors variations of an inter-centroid distance of the minus and plus edges Dg against each temporal axis for Candidates 1 to 5. The graphs illustrated in FIGS. 19A to 19E respectively show the variations of the inter-centroid distance of the minus and plus edges Dg against the temporal axis for Candidates 1 to 5.

For example, as shown in FIG. 19A, Candidate 1 shows little variation of the distance Dg against the temporal axis. As shown in FIG. 19B, Candidate 2 also shows little variation of the distance Dg against the temporal axis. For example, as respectively shown in FIGS. 19C to 19E, Candidate 3 has local minimum values 401 to 403, Candidate 4 has local minimum values 404 to 406, and Candidate 5 has local minimum values 407 to 410.

The eyelid detection apparatus 50 calculates reliability, indicating the probability that the candidate is the subject's eyelid, based on a cycle of local minimum point position of the inter-centroid distance Dg, and/or a distance between the local minimum value and the local maximum value, i.e. amplitude. If the reliability meets predetermined conditions, the candidate is identified as the subject's eyelid. As for the reliability, for example, an inverse number of a sum of amplitude dispersion and cycle dispersion may be employed (parameter calculating mean). In a movement such as the blinking, the amplitude and the cycle stay relatively constant, and the reliability becomes high. On the other hand, in other movements, the amplitude and the cycle usually scatter and the dispersions become large, leading to the low reliability.

The eyelid detection processing executed by the eyelid detection apparatus 50 according to the fourth embodiment of the invention will be described in detail with reference to FIG. 20.

Figure 20:
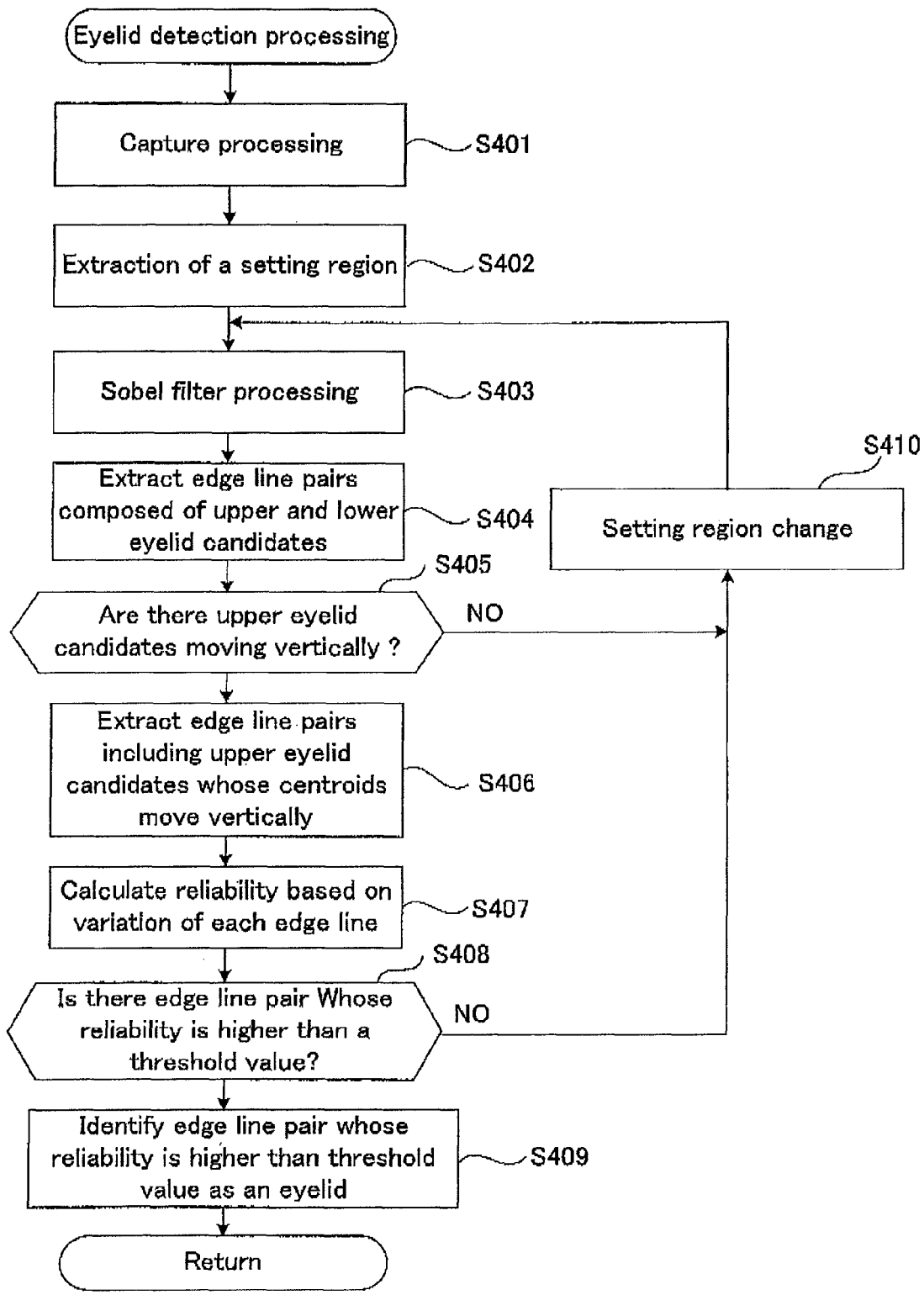
FIG. 20 is a flowchart used for describing eyelid detection processing of the fourth embodiment.

The CPU 24 initiates the processing of FIG. 20 periodically and captures the motion images of the subject's face by the camera 10 via the A/D converter 21 so as to store the captured images in the image memory 22 (Step S401).

The CPU 24 extracts the setting region determined based on the setting information stored in the setting memory 28 from each face image stored in the image memory 22 (Step S402).

The CPU 24 extracts the transverse edge lines from the setting region of the face image by applying the sobel filter for the transverse edge lines (Step S403) stored in the ROM 23.

The CPU 24 extracts the combinations of the minus and plus edges satisfying the formulas (1) to (3) used in the first embodiment from the extracted edge lines (Step S404).

The CPU 24 calculates centroids of the plus and minus edges that are extracted in Step S404. The CPU 24 further calculates a position of the centroid of each plus and minus edge in the face image previously accumulated to create a record of the centroid position of the edge lines extracted in the succession of the face images. Thus, the CPU24 determines whether or not the combination(s) of the plus edge whose centroid moves in the y-axis direction or the direction opposite to the y-axis direction and the minus edge whose centroid does not move (much), is (are) included in the candidates (Step S405).

When the combination of the plus edge whose centroid moves in the y-axis direction or the direction opposite to the y-axis direction and the minus edge whose centroid does not move (much), is not included in the candidates (Step S405; N0), the CPU 24 changes the setting information stored in the setting memory 28 so as to change or expand the setting region (Step S410). Then, the processing returns to Step S402.

When the above-described combination(s) is (are) included in the candidates (Step S405; YES), the CPU 24 extracts the combination(s) of the minus and plus edges (Step S406).

The CPU 24 calculates the reliability of each combination of the minus and plus edges, extracted in Step S406, as described above (Step S407) (reliability calculating means).

The CPU 24 determines whether or not the combination(s) of the minus and plus edges whose reliability is higher than a predetermined value is (are) included in the candidates (Step S408).

When the combination of the minus and plus edges whose reliability is higher than the predetermined value is not included in the candidates (Step S408; NO), the CPU 24 changes the setting information stored in the setting memory 28 so as to change or expand the setting region (Step S410). Then, the processing returns to Step S402.

If the combination(s) of the minus and plus edges whose reliability is higher than the predetermined value is (are) included in the candidates (Step S408; YES), the CPU 24 identifies the combination of the plus and minus edges whose reliability is higher than the predetermined value as the subject's eyelid (Step S409) and terminates the processing.

As just described, similarly to the third embodiment, the eyelid detection apparatus 50 according to the fourth embodiment detects the eyelid correctly with fewer operations even when the subject's mouth and the like are included in the setting region. For example, in the examples shown in FIGS. 18 and 19, Candidate 3, i.e. the combination of the plus edge 303 and the minus edge 304, and Candidate 4, i.e. the combination of the plus edge 307 and the minus edge 308, are detected as the eyelids.

The implementation of the invention is not limited to the aforementioned embodiment, and various kinds of modification and application may be made.

In the third embodiment, the eyelid detection apparatus 50 extracts the combinations of the minus and plus edges and identifies the pairs of the combinations of the moving plus edge and minus edge as the eyelids from the pairs of combinations arranged axisymmetrically with respect to the centerline of the face contour. In the fourth embodiment, the eyelid detection apparatus 50 extracts the combinations of the minus edge and the moving plus edge and calculates the reliability based on the movements of the centroids of the plus and minus edges so as to identify the combination whose reliability is higher than the predetermined value as the eyelid. As applications of the third and fourth embodiments, the eyelid detection apparatus 50 may detect the eyelids by executing the following steps: (1) extracting the combinations of the minus and plus edges, (2) selecting the pairs of the combinations which are arranged axisymmetrically with respect to the centerline of the face contour, (3) calculating the reliability by evaluating the movements of the centroids of the minus and plus edges. The combination of the minus and plus edges whose reliability is higher than the predetermined value is identified as the eyelids (eyelid identifying means).

Alternatively, the eyelid detection apparatus 50 may simply extract edge lines as candidates for the combination of the upper and lower eyelids and identify the pairs of the combinations of the edge lines, which are axisymmetrically arranged with respect to the centerline of the face contour, as the subject's left and right eyelids from the extracted edge lines.

Moreover, in the first to fourth embodiments, the computer 14 performs the eyelid detection processing for the motion images of the subject's face captured by the camera 10. However, the eye detection processing may be performed for motion images of the subject's face captured by an external device other than the camera 10 and stored in the image memory 22. In addition, the eyelid detection processing may be performed for images of plural faces.

According to the above-described embodiments, the eyelid detection apparatus 50 is characterized by storing the plurality of face images of the subject captured at the different timings, detecting the changes in each face image caused by the blinking after processing the plurality of face images stored by the image memory 22, and detecting the position of the eyelid of the subject based on the changes detected.

For example, the eyelid detection apparatus 50 extracts the edge lines, each corresponding to the boundary of the image region after processing the plurality of face images stored by the image memory 22 in Step S101, and further extracts the edge line pairs, which are the candidates for the combination of the edge lines corresponding to the upper and lower eyelids, from the edge lines extracted in Step S103 to identify the edge line pair including the upper eyelid candidate edge line whose representative point moves in the predetermined direction as the combination of the edge lines corresponding to the upper and lower eyelids of the subject from the edge line pairs extracted in Step S104.

For example, the eyelid detection apparatus 50 detects the centerline of the face contour of the subject included in each image stored by the image memory 22 in Step S301 and extracts the edge line pairs, which are the candidates for the combination of the edge lines corresponding to the upper and lower eyelids, from the edge line pairs extracted in Step S305, which are paired with another edge line pair axisymmetrically arranged with respect to the centerline 200 detected in Step S302.

For example, the eyelid detection apparatus 50 calculates the parameter indicating the variations of the distance between the representative point of the edge line corresponding to the upper eyelid and the representative point of the edge line corresponding to the lower eyelid for the edge line pairs extracted in Step S403, and calculates the reliability indicating the probability that the edge line pair is the eyelid of the subject based on the parameter previously calculated. The eyelid detection apparatus 50 detects the edge line pair whose reliability calculated in Step S407 reaches the predetermined value in the edge line pairs extracted in Step S404 and identifies the detected pair as the eyelid of the subject.

For example, the parameter may be at least one of an amplitude and a cycle of the variations of the distance.

For example, the eyelid detection apparatus 50 detects the centerline of the face contour of the subject included in each image stored in the image memory 22. The eyelid detection apparatus 50 calculates the parameter indicating the variations of the distance between the representative point of the edge line corresponding to the upper eyelid and the representative point of the edge line corresponding to the lower eyelid for each edge line pair extracted in the previous step and calculates the reliability indicating the probability that the edge line pair is the edge line pair corresponding to the upper and lower eyelids based on the parameter. Then, the eyelid detection apparatus 50 detects the edge line pair whose reliability reaches the predetermined value from the edge line pairs, each being paired with another edge line pair axisymmetrically arranged with respect to the centerline 200 and identifies the detected edge pair as the edge line pair of the upper and lower eyelids of the subject.

The detection processing may be performed after normalizing at least one of the size (longitudinal and lateral), the gray level, the colors of each face image and the like.

For example, the eyelid detection apparatus 50 detects the face region in each face image stored by the image memory 22 and normalizes the face regions detected in Step S220 to be the predetermined size for creating the face region images. The face region images created in Step S230 are stored, and the differences between the latest face region image and other face region images are taken for creating the difference images. The eyelid detection apparatus 50 detects the regions, each having the gray level value higher than or equal to the predetermined value, as the active regions in each of the difference images, and selects the difference image whose active region is detected as the largest active region from the difference images. Thereafter, the eyelid detection apparatus 50 identifies the eye region from the active regions of the difference image selected in the previous step.

For example, the eye region may be identified based on the left-right symmetry of the active region.

For example, the normalized face region images may be stored for the time period set based on the time period required for the human to close his/her eye.

For example, the eyelid detection apparatus 50 according to the embodiment stores the face images of the subject and extracts the edge lines from the predetermined region of each face image stored in the image memory 22 based on the gray level of the image. Then, the eyelid detection apparatus 50 extracts the edge line pairs, which are the candidates for the combination of the edge lines corresponding to the upper and lower eyelids, from the edge lines extracted in the previous step. The eyelid detection apparatus 50 detects the centerline of the face contour included in each image stored in the image memory 20 and further detects the edge line pairs, each of the edge line pairs being paired with another edge line pair axisymmetrically arranged with respect to the centerline, for identifying the detected edge line pairs as the combination of the edge lines corresponding to the upper and lower eyelids of the subject.

A program according to the embodiment of the invention is characterized by functioning the computer 14 as follows: (1) storing the plurality of the face images of the subject captured at the different timings; (2) extracting the edge lines, each corresponding to the boundary of each image region, after processing the face images stored by the image memory 22; (3) extracting the edge line pairs, which are the candidates for the combination of the edge lines corresponding to the upper and lower eyelids, from the edge lines extracted in Step S104; and (4) identifying the edge line pair having the upper eyelid candidate edge line whose representative point moves in the predetermined direction as the edge line pair corresponding to the upper and lower eyelids of the subject, from the edge line pairs extracted in Step S104.

A program according to the embodiment is characterized by function the computer 14 as follows: (1) storing the plurality of the face images of the subject captured at the different timings; (2) extracting the edge lines from the predetermined region of each image stored by the image memory 22 based on the gray-scale of the image; (3) extracting the edge line pairs, which are the candidates for the edge lines corresponding to the upper and lower eyelids, from the edge lines extracted in Step S305; (4) detecting the centerline of the face contour included in each image stored in the image memory; (5) detecting the edge line pairs extracted in Step S307, which are the edge line pairs being paired with another edge line pair axisymmetrically arranged with respect to the centerline 200 from the edge line pairs extracted in Step S306 and identifying the detected edge line pairs as the combination of the edge lines corresponding to the upper and lower eyelids of the subject.

A program according to the embodiment is characterized by functioning the computer 14 as follows: (1) storing the images including the face of the subject; (2) detecting the face region in each image stored by the image storing means; (3) normalizing the face regions detected in Step S220 to be the predetermined size and creating the face region images; (4) storing the face region images created in Step S230; (5) creating the difference images by taking the differences between the latest face region image and other face region images accumulated in Step S240; (6) detecting regions, each having the gray level value higher than or equal to the predetermined value, as the active regions from each of the difference images; (7) selecting the difference image whose active region is detected as the largest active region in Step S260 in the difference images; and (8) identifying the eye region from the active regions of the difference image selected in Step S270.

According to the embodiments of the invention, the eyelid detection apparatus, which detects the eyelid correctly with few operations, and the programs therefore are provided.

The principles, of the preferred embodiments and mode of operation of the present invention have been described in the foregoing specification. However, the invention, which is intended to be protected, is not to be construed as limited to the particular embodiment disclosed. Further, the embodiment described herein are to be regarded as illustrative rather than restrictive. Variations and changes may be made by others, and equivalents employed, without departing from the spirit of the present invention. Accordingly, it is expressly intended that all such variations, changes and equivalents that fall within the spirit and scope of the present invention as defined in the claims, be embraced thereby.

The invention claimed is:

1. An eyelid detection apparatus, comprising:
a face image storing means storing a plurality of face images of a subject captured at different timings;
a change detecting means detecting changes in each face image caused by blinking after processing the plurality of face images stored by the face image storing means;
an eyelid detecting means detecting a position of an eyelid of the subject based on the changes detected by the change detecting means;
an edge line extracting means extracting edge lines, each corresponding to a boundary of an image region, after processing the plurality of face images stored by the face image storing means; and
an eyelid candidate extracting means extracting edge line pairs, which are candidates for a combination of edge lines corresponding to upper and lower eyelids, from the edge lines extracted by the edge line extracting means, wherein
the eyelid detecting means comprises an eyelid identifying means identifying an edge line pair including an upper eyelid candidate edge line whose representative point moves in a predetermined direction as the combination of the edge lines corresponding to the upper and lower eyelids of the subject, from the edge line pairs extracted by the eyelid candidate extracting means.

2. An eyelid detection apparatus according to claim 1, further comprising:
a centerline detecting means detecting a centerline of a face contour of the subject included in each image stored by the face image storing means;
wherein the eyelid candidate extracting means extracts edge line pairs, which are candidates for the combination of the edge lines corresponding to the upper and lower eyelids, from the edge line pairs extracted by the edge line extracting means, each of the edge line pair being paired with another edge line pair axisymmetrically arranged with respect to the centerline detected by the centerline detecting means.

3. An eyelid detection apparatus according to claim 1, wherein the change detecting means further comprises:
a parameter calculating means calculating a parameter indicating variations of a distance between the representative point of the edge line corresponding to the upper eyelid and a representative point of the edge line corresponding to the lower eyelid for the edge line pairs extracted by the eyelid candidate extracting means; and
a reliability calculating means calculating reliability indicating a probability that an edge line pair is the eyelid of the subject based on the parameter calculated by the parameter calculating means, wherein the eyelid identifying means detects an edge line pair whose reliability calculated by the reliability calculating means reaches a predetermined value in the edge line pairs extracted by the eyelid candidate extracting means and identifies the detected pair as the eyelid of the subject.

4. An eyelid detection apparatus according to claim 3, wherein the parameter is at least one of an amplitude and a cycle of the variations of the distance.

5. An eyelid detection apparatus according to claim 1, further comprising:
a detecting means detecting a centerline of a face contour of the subject included in each image stored by the face image storing means,
wherein the change detection means comprises:
a parameter calculating means calculating a parameter indicating variations of a distance between the representative point of the edge line corresponding to the upper eyelid and a representative point of the edge line corresponding to the lower eyelid for each edge line pair extracted by the eyelid candidate extracting means; and
a reliability calculating means calculating reliability indicating a probability that an edge line pair is the edge line pair corresponding to the upper and lower eyelids based on the parameter based on the parameter calculating means,
wherein the eyelid identifying means detects an edge line pair whose reliability calculated by the reliability calculating means reaches a predetermined value in the edge line pairs, each of the edge line pair being paired with another edge line pair axisymmetrically arranged with respect to the centerline detected by the detecting means and selected from the edge line pairs extracted by the edge line extracting means, and identifies the detected edge pair as the edge line pair of the upper and lower eyelids of the subject.

6. An eyelid detection apparatus according to claim 1, further comprising:
a normalization means normalizing at least one of size and a gray level of each face image stored by the face image storing means.

7. An eyelid detection apparatus according to claim 1, wherein the change detecting means further comprises:
a face region detecting means detecting a face region in each face image stored by the face image storing means;
a normalization means normalizing the face regions detected by the face region detecting means to be a predetermined size and creating face region images;

a normalized image storing means storing the face region images created by the normalization means;

a difference image creating means taking differences between a latest face region image and other face region images and creating difference images; and an active region detecting means detecting regions, each having a gray level value higher than or equal to a predetermined value, as active regions from each of the difference images, wherein the eyelid detecting means comprises a difference image selecting means selecting a difference image whose active region is detected as a largest active region by the active region detecting means in the difference images and an eye region identifying means identifying an eye region from the active regions of the difference image selected by the difference image selecting means.

8. An eyelid detection apparatus according to claim 7, wherein the eye region identifying means identifies the eye region based on left-right symmetry of the active region.

9. An eyelid detection apparatus according to claim 7, wherein the normalized image storing means stores the face region images for a time period set based on a time period required for a human to close an eye.

* * * * *